United States Patent [19]
Suga et al.

[11] Patent Number: 6,037,154
[45] Date of Patent: Mar. 14, 2000

[54] METHOD OF PRODUCING L-SERINE BY FERMENTATION

[75] Inventors: Mikiko Suga; Masakazu Sugimoto, both of Kawasaki; Tsuyoshi Osumi, Tokyo; Tsuyoshi Nakamatsu; Wataru Hibino, both of Kawasaki; Mika Ito, Yokkaichi, all of Japan

[73] Assignee: Ajinomoto Co., Inc., Tokyo, Japan

[21] Appl. No.: 09/222,817

[22] Filed: Dec. 30, 1998

[30] Foreign Application Priority Data

Jan. 12, 1998 [JP] Japan .................................. 10-003751
Dec. 11, 1998 [JP] Japan .................................. 10-353521

[51] Int. Cl.⁷ .............................. C12P 13/06; C12N 9/14; C12N 1/20; C12N 1/12
[52] U.S. Cl. ................. 435/116; 435/252.32; 435/252.1; 435/193; 435/195
[58] Field of Search ..................................... 435/193, 195, 435/252.1, 252.32, 116; 536/23.2

[56] References Cited

PUBLICATIONS

Fell et al., Biochem. J., 256, 97–101, Oct. 1988.

*Primary Examiner*—Robert A. Wax
*Assistant Examiner*—M. Monshipouri
*Attorney, Agent, or Firm*—Oblon, Spivak, McClelland, Maier & Neustadt, P.C.

[57] ABSTRACT

L-serine is produced by cultivating in a medium a coryneform bacterium having L-serine productivity in which an activity of at least one of phosphoserine phosphatase and phosphoserine transaminase is enhanced, preferably, further having introduced therein a gene coding for D-3-phosophoglycerate dehydrogenase in which feedback inhibition by L-serine is desensitized, allowing L-serine to accumulate in the medium, and collecting the L-serine from the medium.

22 Claims, 5 Drawing Sheets

METHOD OF PRODUCING L-SERINE BY FERMENTATION

FIELD OF THE INVENTION

The present invention relates to a method of producing L-serine for use in the production of amino acid mixtures utilized in the field of pharmaceuticals, chemicals, and cosmetics and to coryneform bacteria constituting the method.

BACKGROUND OF THE INVENTION

As a conventional method of producing L-serine by fermentation, there has been reported the method in which a bacterial strain capable of converting glycine and sugar into L-serine is used in a medium containing 30 g/L of glycine to produce at most 14 g/L of L-serine. The conversion yield of glycine into L-serine by this method amounted to 46% (Kubota K. Agricultural Biological Chemistry, 49, 7–12 (1985)). Using a bacterial strain capable of converting glycine and methanol into L-serine, 53 g/L of L-serine can be produced from 100 g/L of glycine (T. Yoshida et al., Journal of Fermentation and Bioengineering, Vol. 79, No. 2, 181–183, 1995). In the method using a bacterium belonging to the genus Nocardia, it has been known that the L-serine productivity of the bacterium can be improved by breeding those strains resistant to serine hydroxamate, azaserine or the like (Japanese Patent Publication No. 57-1235). However, these methods involve use of glycine that is a precursor of L-serine and include complicated operation and is disadvantageous from the viewpoint of costs.

As strains that can ferment L-serine directly from a sugar and do not need addition of the precursor of L-serine to the medium, there has been known *Corynebacterium glutamicum* that is resistant to D-serine, α-methylserine, o-methylserine, isoserine, serine hydroxamate, and 3-chloroalanine but the accumulation of L-serine is as low as 0.8 g/L (Nogei Kagakukaishi, Vol. 48, No. 3, p201–208, 1974). Accordingly, a further strain improvements of are needed for direct fermentation of L-serine on an industrial scale.

On the other hand, regarding coryneform bacteria, there have been disclosed a vector plasmid that is capable of autonomous replication in the cell and having a drug resistance marker gene (cf. U.S. Pat. No. 4,514,502) and a method of introducing a gene into the cell (Japanese Patent Application Laid-open No. 2-207791), and the possibility of growing L-threonine or L-isoleucine producing bacteria (U.S. Pat. Nos. 4,452,890 and 4,442,208). Also, regarding the growth of L-lysine producing bacteria, there has been known a technology involving the incorporation of a gene participating in the biosynthesis of L-lysine into a vector plasmid and the amplification of the plasmid in the cell (Japanese Patent Application Laid-open No. 56-160997).

In the case of *Escherichia coli*, the enzymes participating in the biosynthesis of L-serine include an enzyme that is susceptible to feedback inhibition relative to L-serine production in the wild type and an example has been known in which the introduction of a mutant gene that has been mutated so that the feedback inhibition could be desensitized resulted in an enhancement in the L-serine (Japanese Patent No. 2584409). As such genes, there has been known specifically 3-PGDH gene (hereafter, the gene coding for 3-PGDH protein will also be referred to "serA").

Further, in the case of coryneform bacteria, an example has been known in which the amplification of 3-PGDH gene influences the productivity of L-tryptophane (Japanese Patent Application Laid-open No. 3-7591).

SUMMARY OF THE INVENTION

An object of the present invention is to provide a microorganism that converts a sugar into L-serine and to provide a method of accumulating L-serine in a culture medium utilizing the ability of the microorganism to convert the sugar into L-serine, i.e., a method of producing L-serine that is advantageous in practicing on an industrial scale.

As a result of intensive investigation with view to achieving the above object, it has now been discovered by the present inventors that screening a strain in which an activity of at least one of phosphoserine phosphatase and phosphoserine transaminase is enhanced from coryneform bacteria having L-serine productivity, preferably the bacteria deficient in L-serine decomposing activity or a mutant thereof having resistance to an L-serine analogue, and L-serine fermentation using the screened strain will enhance the accumulation of L-serine drastically. The present invention has been completed based on this discovery.

That is, the present invention relates to a coryneform bacterium having L-serine productivity in which an activity of at least one of phosphoserine phosphatase and phosphoserine transaminase is enhanced.

Further, the present invention relates to the coryneform bacterium as described above, which is enhanced the activitise of both phosphoserine phosphatase and phosphoserine transaminase; the coryneform bacterium as described above, having L-serine productivity due to deficiency in L-serine decomposing activity; the coryneform bacterium as described above, having L-serine productivity due to its resistance to L-serine analogue(s); the coryneform bacterium as described above, in which an activity of phosphoserine phosphatase or phosphoserine transaminase is enhanced by increasing a copy number of a gene coding for phosphoserine phosphatase or a gene coding for phosphoserine transaminase in the coryneform bacterium described above in its cell; and the coryneform bacterium as described above, having introduced therein a gene coding for D-3-phosophoglycerate dehydrogenase in which feedback inhibition by L-serine is desensitized.

Further, the present invention relates to a method of producing L-serine, comprising the steps of cultivating the coryneform bacterium as described above in a medium to accumulate L-serine in the medium and collecting the L-serine from the medium.

DETAILED DESCRIPTION OF THE INVENTION

Figure 1:
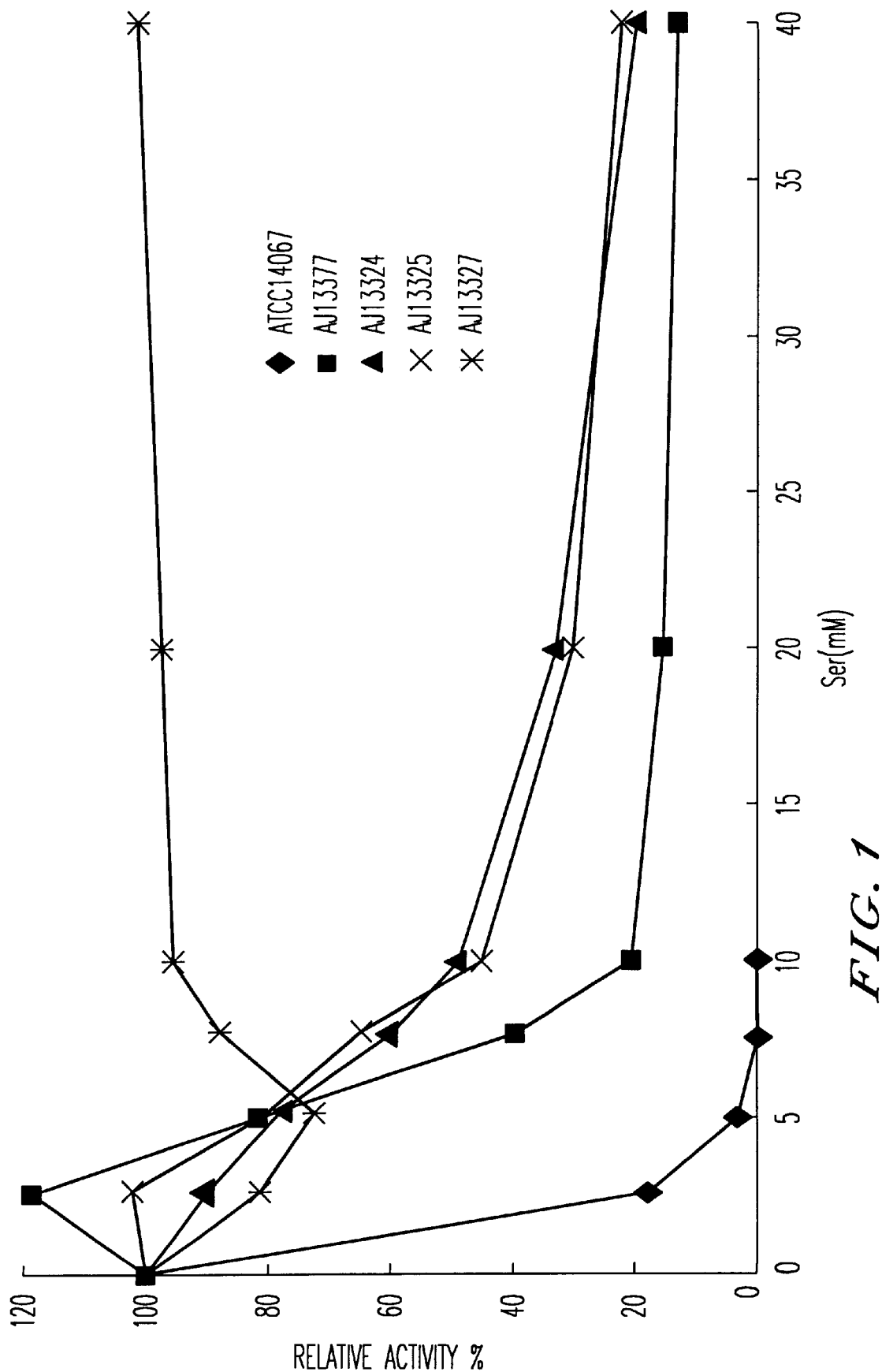
FIG. 1 illustrates a manner of feedback inhibition of 3-PGDH derived from various strains by L-serine. The horizontal axis indicates the concentration of L-serine in the enzyme solution. The vertical axis indicates percentage of the 3-PGDH activity in the presence of L-serine to that in the absence of L-serine. Symbol ♦ illustrates a manner of feedback inhibition of 3-PGDH derived from ATCC14067 strain by L-serine. Symbol ■ illustrates a manner of feedback inhibition of 3-PGDH derived from AJ13377 strain by L-serine. Symbol ▲ illustrates a manner of feedback inhibition of 3-PGDH derived from AJ13324 strain by L-serine. Symbol X illustrates a manner of feedback inhibition of 3-PGDH derived from AJ13325 strain by L-serine. Symbol * illustrates a manner of feedback inhibition of 3-PGDH derived from AJ13327 strain by L-serine.

The coryneform bacteria referred to in the present invention are a group of microorganisms as defined in *Bergey's Manual of Determinative Bacteriology*, 8th ed., p. 599 (1974), which are aerobic Gram-positive rods having no acid resistance and no spore-forming ability. The coryneform bacteria include bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium and bacteria belonging to the genus Microbacterium.

The coryneform bacteria of the present invention are coryneform bacteria that have L-serine productivity in which an activity of phosphoserine phosphatase or phosphoserine transaminase is enhanced. Such bacteria can be obtained, for example, by increasing the copy number of a gene coding for phosphoserine phosphatase (hereafter, referred to as "serB") or a gene coding for phosphoserine transaminase (hereafter, referred to as "serC") in a coryneform bacterial cell having L-serine productivity.

Also, the coryneform bacteria of the present invention can be obtained by imparting L-serine productivity to a coryneform bacterium having an enhanced activity of phosphoserine phosphatase or phosphoserine transaminase.

As the coryneform bacteria having L-serine productivity, there can be cited, for example, coryneform bacterial deficient in L-serine decomposing activity, coryneform bacteria resistant to L-serine analogues, and coryneform bacteria deficient in L-serine decomposing activity and being resistant to L-serine analogues.

In the present invention, the L-serine analogue includes azaserine or B-(2-thienyl)-DL-alanine.

The coryneform bacteria resistant to L-serine analogues and having L-serine productivity, more preferably the coryneform bacteria deficient in L-serine decomposing activity from among them can be artificially mutated or induced using wild type or coryneform bacteria having L-serine productivity as a parent strain.

The coryneform bacteria having resistance to an L-serine analogue, deficient in L-serine decomposing activity, and having L-serine productivity can be collected, for example, as follows. *Brevibacterium flavum* ATCC14067 is subjected to mutation treatment by a conventional method (contact with N-methyl-N'-nitro-N-nitrosoguanidine, etc.) to obtain a mutant that is deficient in L-serine decomposing activity, and then a bacterium resistant to an L-serine analogue such as azaserine or β-(2-thienyl)-DL-alanine is collected from the mutant as a parent strain. Also, after L-serine analogue-resistant bacterium is obtained, a mutant deficient in L-serine decomposing activity may be obtained. Among the mutants obtained by the methods described above, there are strains that accumulate L-serine in high concentrations.

The L-serine analogue-resistant bacteria can be obtained by introducing the mutant serA described later on into a parent strain or L-serine decomposing activity deficient mutant.

By the term "L-serine analogue resistance" is meant the property that a bacterium grows faster than the wild type in a medium containing an L-serine analogue.

More specifically, for example, the term "azaserine resistance" refers to the property that a bacterium grows faster than the wild type in a medium containing azaserine. For example, those strains that form colonies on a solid medium containing 0.25 g/L of azaserine at 30° C. within 4 to 5 days are said to have azaserine resistance.

Similarly, the term "β-(2-thienyl)-DL-alanine resistance" refers to the property that a bacterium grows faster than the wild type in a medium containing β-(2-thienyl)-DL-alanine. For example, those strains that form colonies on a solid medium containing 0.25 g/L of β-(2-thienyl)-DL-alanine at 30° C. within 4 to 5 days are said to have β-(2-thienyl)-DL-alanine resistance.

Next, the enhancement of phosphoserine phosphatase activity or phosphoserine transaminase activity will be described.

The enhancement of phosphoserine phosphatase activity or phosphoserine transaminase activity can be performed by introducing serB or serC each in an expressible form into a coryneform bacterium. This is possible either by forced expression of genes coding for respective enzymes by means of separate promoters or by forced expression of the both genes under the control of a single promoter. Regardless of whether these genes are on a plasmid or chromosome, the expression may be enhanced by enhancement of an expression control sequence such as promoter of a gene, or improvement in translation efficiency. Alternatively, the enzyme activity can be enhanced by amplification of the number of genes on a chromosome. Further, the enhancement of these enzyme activities can be achieved by use of a modified gene coding for phosphoserine phosphatase or phosphoserine transaminase modified in such a manner that a modified enzyme having an increased specific activity is coded for.

In order to introduce serB or serC into a coryneform bacterium, a DNA fragment containing serB or serC may be ligated with a vector that functions in coryneform bacteria to generate a recombinant DNA, followed by introduction of it into a coryneform bacterium host having L-serine productivity to transform it. As a result of an increase in copy number of serB or serC in the cell of transformed strain, the phosphoserine phosphatase activity or phosphoserine transaminase activity thereof is amplified. Introduction of a recombinant DNA containing both serB and serC or both a recombinant DNA containing serB and a recombinant DNA containing serC into a coryneform bacterium will amplify the both phosphoserine phosphatase activity and phosphoserine transaminase activity.

The base sequences of serB and serC are known (serB: GenBank; X03046 M30784, serC: GenBank; D90728). It is possible to synthesize primers based on their base sequences and collect the serB gene or serC gene of these microorganisms by the PCR method using the chromosomal DNA of *Escherichia coli, Brevibacterium flavum* or other microorganisms as a template. As such a primer, there can be cited the primer having the base sequence shown in Sequence ID No. 15 to 18.

It is preferred that serB gene or serC gene is ligated with vector DNA autonomously replicable in cells of *Escherichia coli* and/or coryneform bacteria to prepare recombinant DNA, and the recombinant DNA is introduced into cells of *Escherichia coli* beforehand. Such provision makes following operations easy. The vector autonomously replicable in cells of *Escherichia coli* is preferably a plasmid vector which is preferably autonomously replicable in cells of a host, including, for example, pUC19, pUC18, pBR322, pHSG299, pHSG399, pHSG398, and RSF1010.

In the case where serB gene and serC gene are loaded on separate vectors for introduction into a coryneform bacterium, it is preferred to use two vectors having respective marker genes differing one from another.

Recombinant DNA may be prepared by utilizing transposon (WO 02/02627 International Publication Pamphlet, WO 93/18151 International Publication Pamphlet, European Patent Application Laid-open No. 0445385, Japanese Patent Application Laid-open No. 6-46867, Vertes, A. A. et al., Mol. Microbiol., 11, 739–746 (1994), Bonamy, C., et al., Mol. Microbiol., 14, 571–581 (1994), Vertes, A. A. et al., Mol. Gen. Genet., 245, 397–405 (1994), Jagar, W. et al., FEMS Microbiology Letters, 126, 1–6 (1995), Japanese Patent Application Laid-open No. 7-107976, Japanese Patent Application Laid-open No. 7-327680, etc.), phage vectors, recombination of chromosomes (Experiments in Molecular Genetics, Cold Spring Harbor Laboratory Press (1972); Matsuyama, S. and Mizushima, S., J. Bacteriol., 162, 1196 (1985)) and the like.

When a DNA fragment having an ability to allow a plasmid to be autonomously replicable in coryneform bacteria is inserted into these vectors, they can be used as a so-called shuttle vector autonomously replicable in both *Escherichia coli* and coryneform bacteria.

Such a shuttle vector includes the followings. Microorganisms harboring each of vectors and deposition numbers in international deposition facilities are shown in parentheses.

pHC4: *Escherichia coli* AJ12617 (FERM BP-3532)

pAJ655: *Escherichia coli* AJ11882 (FERM BP-136) *Corynebacterium glutamicum* SR8201 (ATCC 39135)

pAJ1844: *Escherichia coli* AJ11883 (FERM BP-137) *Corynebacterium glutamicum* SR8202 (ATCC 39136)

pAJ611: *Escherichia coli* AJ11884 (FERM BP-138)

pAJ3148: *Corynebacterium glutamicum* SR8203 (ATCC 39137)

pAJ440: *Bacillus subtilis* AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000×g to obtain a supernatant to which polyethylene glycol is added, followed by fractionation and purification by means of cesium chloride-ethidium bromide equilibrium density gradient centrifugation.

*Escherichia coli* can be transformed by introducing a plasmid in accordance with, for example, a method of D. M. Morrison (*Methods in Enzymology*, 68, 326 (1979)) or a method in which recipient cells are treated with calcium chloride to increase permeability for DNA (Mandel, M. and Higa, A., *J. Mol. Biol.*, 53, 159 (1970)).

Introduction of plasmids to coryneform bacteria to cause transformation can be performed by the electric pulse method (Sugimoto et al., Japanese Patent Application Laid-open No. 2-207791).

Examples of the coryneform bacterium used to introduce the DNA described above include, for example, the following wild type strains: *Corynebacterium acetoacidophilum* ATCC 13870; *Corynebacterium acetoglutamicum* ATCC 15806; *Corynebacterium callunae* ATCC 15991; *Corynebacterium glutamicum* ATCC 13032; (*Brevibacterium divaricatum*) ATCC 14020; (*Brevibacterium lactofermentum*) ATCC 13869; (*Corynebacterium lilium*) ATCC 15990; (*Brevibacterium flavum*) ATCC 14067; *Corynebacterium melassecola* ATCC 17965; *Brevibacterium saccharolyticum* ATCC 14066; *Brevibacterium immariophilum* ATCC 14068; *Brevibacterium roseum* ATCC 13825; *Brevibacterium thiogenitalis* ATCC 19240; *Microbacterium ammoniaphilum* ATCC 15354; *Corynebacterium thermoaminogenes* AJ12340 (FERM BP-1539).

Enhancement of phosphoserine phosphatase activity or phosphoserine transaminase activity can also be achieved by introducing multiple copies of the serB gene or serC gene into the chromosomal DNA of the above-described host strains. In order to introduce multiple copies of the serB gene or serC gene in the chromosomal DNA of coryneform bacterium, the homologous recombination is carried out using a sequence whose multiple copies exist in the chromosomal DNA as targets. As sequences whose multiple copies exist in the chromosomal DNA, repetitive DNA, inverted repeats exist at the end of a transposable element can be used. Also, as disclosed in Japanese Patent Publication Laid-Open No. 2-109985, it is possible to incorporate the serB gene or serC gene into transposon, and allow it to be transferred to introduce multiple copies of the serB gene or serC gene into the chromosomal DNA. By either method, the number of copies of the serB gene or serC gene within cells of the transformant strain increases, and as a result, phosphoserine phosphatase activity or phosphoserine transaminase activity is enhanced.

Other than the above-described gene amplification, enhancement of phosphoserine phosphatase activity or phosphoserine transaminase activity can also be achieved by substituting the expression regulation sequence such as promoter of the serB gene or serC gene with a more potent one. For example, lac promoter, trp promoter, trc promoter, tac promoter, and $P_R$ promoter and $P_L$ promoter of lambda phage are known as potent promoters. By substituting the promoter inherent in serB gene or serC gene with these promoters, the expression of serB gene or serC gene is enhanced, thereby enhancing phosphoserine phosphatase activity or phosphoserine transaminase activity.

In a preferred embodiment, the coryneform bacteria of the present invention is a strain obtained by introducing a gene coding for D-3-phosphoglycerate dehydrogenase (hereafter, also referred to as "3-PGDH") in which feedback inhibition by L-serine is desensitized, into a coryneform bacterium having L-serine productivity and an enhanced activity of phosphoserine phosphatase or phosphoserine transaminase.

3-PGDH catalyzes reaction in which 3-phosphoglycerate is oxidized into 3-phosphohydroxylpyruvic acid in the presence of nicotinamide adenine dinucleotide (NAD) as a coenzyme.

3-PGDH derived from a wild type coryneform bacterium is susceptible to feedback inhibition by L-serine and its activity is almost completely inhibited in the presence of 10 mM of L-serine. By the term "3-PGDH in which feedback inhibition by L-serine is desensitized," is meant 3-PGDH having 20% or more, preferably 40% or more, more preferably 90% or more of the activity in the absence of L-serine even in the presence of 10 mM of L-serine. 3-PGDH derived from *Brevibacterium flavum* AJ13327 described in the examples hereinbelow retains substantially 100% of the activity in the presence of 80 mM of L-serine and therefore one of the most preferred 3-PGDHs.

The gene coding for 3-PGDH in which feedback inhibition by L-serine is desensitized can be prepared from the chromosomal DNA of L-serine analogue resistant coryneform bacteria, for example, azaserine resistant strain AJ13327 of *Brevibacterium flavum* obtained in the examples described below.

3-PGDH derived from a wild type coryneform bacterium (hereafter, DNA coding for this is also referred to as "wild type serA") has the amino acid sequence described by SEQ ID NO: 12 in the Sequence Listing. Specific examples of the 3-PGDH in which feedback inhibition by L-serine is desensitized (hereafter, DNA coding for this is also referred to as "mutant serA") include D-3-phosphoglycerate dehydrogenase characterized in that in D-3-phosphoglycerate dehydrogenase having the amino acid sequence described by SEQ ID NO: 12 in the Sequence Listing or the same amino acid sequence as above but has substitution, addition or deletion of one or more amino acids, the amino acid residue corresponding to the 325th glutamic acid residue of the amino acid sequence in the SEQ ID NO: 12 has been substituted by other amino acid. Most preferred as the other amino acid residue is a lysine residue.

The DNA fragment containing serA gene from a coryneform bacterium can be isolated, for example, by preparing chromosomal DNA according to the method of Saito and Miura (H. Saito and K. Miura, Biochem. Biophys. Acta, 72, 619 (1963)) or the like and then amplifying serA gene by polymerase chain reaction method (PCR: polymerase chain reaction; cf. White, T. J. et al.; Trends Genet. 5, 185 (1989)). For example, in order to amplify DNA fragment containing ORF (172 to 1705) of SEQ ID NO : 11 in the Sequence Listing, any 20 to 30 bases are selected from the region from the first base in SEQ ID NO: 11 to the base immediately before ATG to obtain one primer. Further, any 20 to 30 bases are selected from the region from the base immediately after the termination codon to the last base in SEQ ID NO: 11 to obtain another primer.

When serA is isolated from a wild type strain of 3-PGDH, wild type serA is obtained and isolation of serA from a mutant retaining 3-PGDH in which feedback inhibition by L-serine is desensitized (3-PGDH mutant) gives mutant serA. Specifically, the wild type serA has the sequence described by SEQ ID NO: 11 in the Sequence Listing, and mutant serA has the sequence described by SEQ ID NO: 13 in the Sequence Listing.

The mutant serA may be introduced into a coryneform bacterium by transformation of the coryneform bacterium with a mutant serA-containing recombinant vector in the same manner as in the introduction of serB or serC. The mutant serA is preferably introduced in multiple copies. The mutant serA and serB or serC may be loaded on a single vector or on separate two or three vectors, respectively.

For L-serine production using the strain of the present invention, the following methods may be used. As the medium to be used, there can be used conventional liquid mediums containing carbon sources, nitrogen sources, inorganic salts, and optionally organic trace nutrients such as amino acids, vitamins, etc., if desired.

As carbon sources, it is possible to use sugars such as glucose, sucrose, fructose, galactose; saccharified starch solutions, sweet potato molasses, sugar beet molasses and hightest molasses which are including the sugars described above; organic acids such as acetic acid; alcohols such as ethanol; glycerol and the like.

As nitrogen sources, it is possible to use ammonia gas, aqueous ammonia, ammonium salts, urea, nitrates and the like. Further, organic nitrogen sources for supplemental use, for example, oil cakes, soybean hydrolysate liquids, decomposed casein, other amino acids, corn steep liquor, yeast or yeast extract, peptides such as peptone, and the like, may be used.

As inorganic ions, phosphoric ion, magnesium ion, calcium ion, iron ion, manganese ion and the like may be added optionally.

In case of using the microorganism of the present invention which requires nutrients such as amino acids for its growth, the required nutrients should be supplemented.

The microorganisms are incubated usually under aerobic conditions at pH 5 to 8 and temperature ranges of 25 to 40° C. The pH of the culture medium is controlled at a predetermined value within the above-described ranges depending on the presence or absence of inorganic or organic acids, alkaline substances, urea, calcium carbonate, ammonia gas, and the like.

L-Serine can be collected from the fermentation liquid, for example, by separating and removing the cells, subjecting to ion exchange resin treatment, concentration cooling crystallization, membrane separation, and other known methods in any suitable combination. In order to remove impurities, activated carbon adsorption and recrystallization may be used for purification.

The present invention provides a coryneform bacterium that synthesizes L-serine from a sugar. The coryneform bacterium can be utilized in a method of producing L-serine that is advantageous industrially.

DESCRIPTION OF PREFERRED EMBODIMENTS

Example 1

Construction of L-serine producing bacteria *Brevibacterium flavum* AJ13324 and AJ13327

*Brevibacterium flavum* AJ13324 and AJ13327 were constructed from *Brevibacterium flavum* AJ13377 that is deficient in L-serine decomposing activity obtained from wild type strain *Brevibacterium flavum* ATCC 14067.

To obtain a mutant, cells proliferated for 24 hours in a bouillon medium (a medium containing 1 g of fish meat extract, 1 g of polypeptone, 0.5 g of yeast extract, and 0.5 g of sodium chloride in 1 liter of water, adjusted to pH 7.0) were suspended in 100 mM phosphate buffer (pH 7.0) (containing $10^9$ to $10^{10}$ cells/ml). NG (N-methyl-N'-nitro-N-nitrosoguanidine) was added to the suspension to a concentration of 200 μg/ml and left to stand at 30° C. for 30 minutes. The thus NG treated cells were washed well with the above-described buffer.

To select strains having no L-serine decomposing activity from the NG treated cells, NG treated cells of *Brevibacterium flavum* ATCC 14067 after washed were spread on a bouillon agar medium and incubated at 30° C. for 24 hours to allow colony formation. Then, the colonies on the bouillon agar medium were used as a negative and replica formation was performed on a minimal medium and a minimal medium for selection. Then, strains were screened that grow on the minimal medium but do not grow on the minimal medium for selection. The minimal medium was a medium that contained 20 g of glucose, 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetrato pentahydrate, 50 μg of biotin, 200 μg of thiamin hydrochloride, 200 μg of nicotinic acid amide, and 2.0 g of agar per liter of distilled water. The minimal medium for selection was a medium that contained 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetrato pentahydrate, 50 μg of biotin, 200 μg of thiamin hydrochloride, 200 μg of nicotinic acid amide, 0.5 g of L-serine and 2.0 g of agar per liter of distilled water. Among the mutants obtained by this method were found many strains that have no L-serine decomposing activity and *Brevibacterium flavum* AJ13377 was obtained as one of such strains.

To select azaserine resistant strains from NG treated strains using *Brevibacterium flavum* AJ13377 as a parent strain, NG treated *Brevibacterium flavum* AJ13377 cells after washed were inoculated on a minimal medium for selection. The minimal medium for selection was a medium that contained 20 g of glucose, 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetra- to pentahydrate, 50 μg of biotin, 200 μg of thiamin hydrochloride, 200 μg of nicotinic acid amide, and 250 mg of azaserine per liter of distilled water. The NG treated mutant was incubated in the above-described medium at 30° C. for 5 to 10 days. The cell culture thus obtained was spread on a bouillon agar medium and incubated at 30° C. for 24 hours for colony formation. Azaserine resistant strains were obtained from the strains that formed colonies. The mutants thus obtained included many strains that accumulated L-serine in considerable amounts at high yields. From the strains were obtained two strains, i.e., *Brevibacterium flavum* AJ13324 and AJ13327. It was confirmed that these strains were able to grow in the presence of 0.25 g/L of azaserine.

Example 2
Construction of novel L-serine producing bacterium *Brevibacterium flavum* AJ13325

*Brevibacterium flavum* AJ13325 was constructed from *Brevibacterium flavum* AJ13377 lacking L-serine decomposing activity, which was obtained from the wild type strain *Brevibacterium flavum* ATCC 14067.

To select β-(2-thienyl)-DL-alanine resistant strains from NG treated strains using *Brevibacterium flavum* AJ13377 as a parent strain, *Brevibacterium flavum* AJ13377 cells were NG treated and washed before their inoculation on a minimal medium for selection. The minimal medium for selection was a medium that contained 20 g of glucose, 1 g of ammonium sulfate, 1 g of potassium dihydrogen phosphate, 2.5 g of urea, 0.4 g of magnesium sulfate heptahydrate, 0.01 g of iron (II) sulfate heptahydrate, 0.01 g of manganese sulfate tetra- to pentahydrate, 50 μg of biotin, 200 μg of thiamin hydrochloride, 200 μg of nicotinic acid amide, and 250 mg of β-(2-thienyl)-DL-alanine per liter of distilled water. The NG treated mutant was incubated in the above-described medium at 30° C. for 5 to 10 days. The cell culture thus obtained was spread on a bouillon agar medium and incubated at 30° C. for 24 hours for colony formation. β-(2-Thienyl)-DL-alanine resistant strains were obtained from the strains that formed colonies. The mutants thus obtained included many strains that accumulated L-serine in considerable amounts at high yields. *Brevibacterium flavum* AJ13325 was obtained as one of such strains. It was confirmed that these strains were able to grow in the presence of 0.25 g/L of β-(2-thienyl)-DL-alanine.

Example 3
Production of L-serine by L-serine producing bacteria *Brevibacterium flavum* AJ13324, AJ13325 and AJ13327

*Brevibacterium flavum* AJ13324, AJ13325 and AJ13327 were each incubated on a bouillon agar medium at 30° C. for 24 hours and a loopful of each microorganism was inoculated in a 500 ml shaking flask containing 20 ml of a fermentation medium having the composition shown in Table 1. As a control, the parent strains *Brevibacterium flavum* ATCC 14067 and AJ13377 were inoculated as a same manner as described above. The medium was adjusted to pH 7.0 with potassium hydroxide and autoclaved at 115° C. for 15 minutes. After the sterilization and cooling, calcium carbonate that had been dry air sterilized at 180° C. for 3 hours was added in an amount of 5 g/L.

TABLE 1

| Component | Content/liter |
| --- | --- |
| Glucose | 110.0 g |
| Potassium dihydrogen phosphate | 0.4 g |
| Magnesium sulfate heptahydrate | 0.4 g |
| Iron (II) sulfate heptahydrate | 0.01 g |
| Manganese sulfate tetra- to pentahydrate | 0.01 g |
| Ammonium sulfate | 25.0 g |
| Thiamin hydrochloride | 100 μg |
| Biotin | 100 μg |
| Soy bean protein hydrochloric acid hydrolysate ("Mieki" (registered trademark) | 40 ml |
| pH | 7.0 |

Determination of L-serine using high performance liquid chromatography (Hitachi L-8500 Amino Acid Autoanalyzer) revealed that *Brevibacterium flavum* AJ13324, AJ13325 and AJ13327 accumulated L-serine in the medium in amounts of 15.2 g/L, 14.3 g/L, and 15.4 g/L, respectively. On the other hand, *Brevibacterium flavum* strains ATCC 14067 and AJ13377 incubated as a control accumulated L-serine in amounts of 0 g/L and 5.0 g/L, respectively.

The culture broth of *Brevibacterium flavum* AJ13324 was centrifuged and the supernatant was subjected to desalting treatment using cation exchange resin, followed by chromatographic separation with cation exchange resin and anion exchange resin to remove byproducts and purification by crystallization to obtain L-serine crystals of at least 99% purity at a yield from broth of 55%.

Example 4
Measurement of 3-PGDH activity

*Brevibacterium flavum* AJ13324, AJ13325 and AJ13327 were each incubated on a bouillon agar medium at 30° C. for 24 hours and a loopful of each microorganism was inoculated in a 500 ml shaking flask containing 50 ml of a fermentation medium having the composition shown in Table 2. As a control, the parent strains *Brevibacterium flavum* ATCC 14067 and AJ13377 were inoculated as a same manner as described above. The medium for inoculation was adjusted to pH 5.5 with sodium hydroxide and autoclaved at 115° C. for 15 minutes.

TABLE 2

| Component | Content/liter |
| --- | --- |
| Glucose | 30.0 g |
| Potassium dihydrogen phosphate | 1.0 g |
| Magnesium sulfate heptahydrate | 0.4 g |
| Iron (II) sulfate heptahydrate | 0.01 g |
| Manganese sulfate tetra- to pentahydrate | 0.01 g |
| Ammonium sulfate | 3.0 g |
| Soy bean protein hydrochloric acid hydrolysate ("Mieki" (registered trademark) | 3.0 ml |
| Thiamin hydrochloride | 200 μg |

TABLE 2-continued

| Component | Content/liter |
| --- | --- |
| Biotin | 50 μg |
| Urea | 3.0 g |
| Yeast extract | 2.0 g |
| pH | 5.5 |

After collecting cells from the culture broth of each strain, the cells were washed twice with physiological saline and suspended in 50 mM sodium phosphate buffer (pH 7.0) containing 2 mM dithiothreitol. After ice cooling, the suspension was subjected to a sonicator to fragment the cells and the resulting liquid was ultracentrifuged. The ultracentrifugaton was run at 45,000 rpm for 1 hour to obtain a crude enzyme solution.

The enzyme activity of 3-PGDH was measured by the method of Salach H. J. et al. (Method in Enzymology, vol 9, 216–220 (1966)).

More specifically, 0.4 ml of 0.015 M NAD, 0.12 ml of 0.25 M EDTA (pH 9, NaOH), 0.1 ml of 0.05 M glutathione (pH 6, KOH), 0.5 ml of 1 M hydrazine (pH 9, acetate), 0.6 ml of 1 M Tris (pH 9, HCl), a suitable concentration of L-serine (0 to 40 mM), and water to make 2.3 ml, warmed to 25° C. in advance, were added. Then, 0.2 ml of the crude enzyme solution was added and the temperature was kept the same for 5 minutes. Thereafter, 0.5 ml of 0.1 M 3-PGA (3-phosphoglycerate disodium salt, pH 7, NaOH) was added. After stirring, the absorbance at 340 nm of the reaction mixture was measured for 30 seconds. The reaction was carried out at 25° C.

For the measurement of activity, Hitachi U-2000A spectrophotometer was used.

FIG. 1 illustrates the results obtained. AJ13377 strain was relieved of L-serine sensitivity as compared with the wild type strain ATCC 14067. The AJ13324 strain was more relieved of L-serine sensitivity and the AJ13325 strain was of the same level as the AJ13324 strain in this respect. The AJ13327 strain was relieved of L-serine sensitivity greatly. And the inhibition was completely desensitized even in the presence of 80 mM L-serine.

Although some examples of desensitization of the inhibition of 3-PGDH by L-serine were reported on *Escherichia coli* (Tosa and Pizer, J. Bacteriol. 106: 972–982 (1971) or Japanese Patent Application Laid-open No. 6-510911), there has been known no example of complete desensitization of the inhibition in the presence of such a high concentration of L-serine.

Example 5

Cloning of coryneform bacteria-derived wild type and mutant serA

As shown in Example 4, the feedback inhibition by L-serine was completely desensitized in the AJ13327 strain. Accordingly, cloning of serA gene coding for wild type 3-PGDH derived from the ATCC 14067 strain and mutant 3-PGDH derived from the AJ13327 strain was attempted in order to elucidate what the variation was like and confirm the amplification effect of 3-PGDH.

To amplify serA from the chromosome of *Brevibacterium flavum* using a PCR method, it is necessary to make a corresponding primer. Since no report has been made on the cloning and nucleotide sequence of serA of *Brevibacterium flavum*, the sequence of serA derived from Corynebacterium was used. Plasmid pDTS9901 was extracted from the strain *Corynebacterium glutamicum* K82 (cf. FERM BP-2444 and Japanese Patent Application Laid-open No. 3-7591) in which the serA fragment derived from Corynebacterium was cloned using Wizard Minipreps DNA Purification System (manufactured by Promega) and a DNA fragment of about 1.4 kb containing serA was cleaved with restriction enzyme BamHI (manufactured by Takara Shuzo Co., Ltd.).

Figure 2:
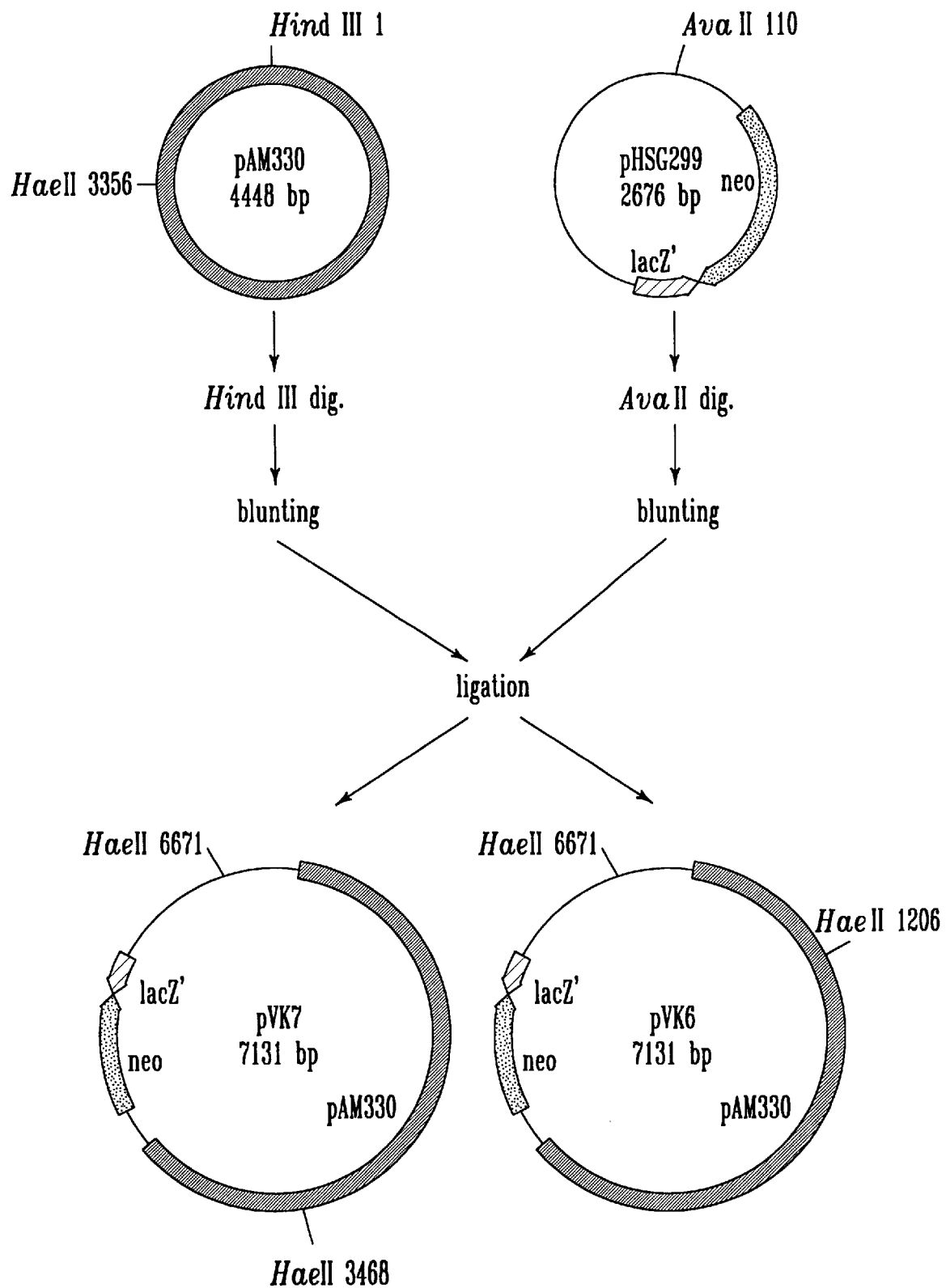
FIG. 2 illustrates the construction of plasmids pVK7 and pVK6.

As a vector for cloning the gene fragment, there was used a newly constructed cloning vector pVK7 for coryneform bacteria.

pVK7 was constructed by ligating (a cloning vector for *Escherichia coli*) pHSG299 (Kmr; Takeshita, S. et al., Gene, 61, 63–74 (1987), Japanese Patent Application Laid-open No. 10-215883), to pAM330, a cryptic plasmid of *Brevibacterium lactofermentum*, in the manner described below. pHSG299 was cleaved with monospecific restriction enzyme AvaII (manufactured by Takara Shuzo Co., Ltd.) and blunt ended with T4 DNA polymerase. This was ligated with pAM330 that had been cleaved with HindIII (manufactured by Takara Shuzo Co., Ltd.) and blunt ended with T4 DNA polymerase. The two types of plasmids obtained were designated pVK6 and pVK7 depending on the direction of pAM330 insertion relative to pHSG299, and pVK7 was used in the following experiments. pVK7 was capable of autonomous replication in *Escherichia coli* and *Brevibacterium lactofermentum* and retains the multiple cloning site and lacZ' derived from pHSG299. FIG. 2 illustrates the process of constructing pVK6 and pVK7.

To the shuttle vector pVK7 thus constructed was ligated a DNA fragment of about 1.4 kb containing serA. pDTS9901 was cleaved with restriction enzyme BamHI (manufactured by Takara Shuzo Co., Ltd.) and ligated to pVK7 also cleaved with restriction enzyme BamHI. The ligation of DNA was performed using DNA Ligation Kit (manufactured by Takara Shuzo Co., Ltd.) according to the prescribed method.

For the sequencing reaction, use was made of PCR thermal cycler MP type (manufactured by Takara Shuzo Co., Ltd.) and of Dye Terminator Cycle Sequencing FS Ready Reaction Kit (manufactured by Perkin Elmer). As the DNA primer, there were used M13(-21), RV primer (manufactured by Takara Shuzo Co., Ltd.). The SEQ ID NO: 1 in the Sequence Listing shows the sequence thus obtained. SEQ ID NO: 2 shows an amino acid sequence that can be coded for by this sequence.

A primer was synthesized based on the base sequence thus determined and serA was amplified by a PCR method using the chromosomal DNA of the mutant *Brevibacterium flavum* AJ13327 as a template. The SEQ ID NOS: 3 and 4 in the Sequence Listing show the N-terminal side and C terminal side sequences, respectively, of the DNA primer that were synthesized for gene amplification.

In the preparation of the chromosomal DNA of *Brevibacterium flavum*, use is made of Genomic DNA Purification Kit (Bacterial) (manufactured by Advanced Genetic Technologies Corp.) and the preparation method was according to the annexed protocol.

For the PCR reaction, use is made of PCR Thermal Cycler MP type (Takara Shuzo Co., Ltd.) and of TaKaRa Taq (manufactured by Takara Shuzo Co., Ltd.).

The PCR product was ligated directly to plasmid pCR2.1 vector using Original TA Cloning Kit (manufactured by Invitrogen) and transformation was performed using competent cell of INVαF'. The transformed cells were spread on L medium (10 g/L of bactotryptone, 5 g/L of bactoyeast extract, 15 g/L of NaCl, and 15 g/L of agar) further containing 40 μg/ml of X-Gal (5-bromo-4-chloro-3-indolyl-β-D-galactoside) and 25 μg/ml of Kanamycin, and incubated overnight. The white colonies, which appeared, were collected and separated to single colonies to obtain a transformed strain.

Plasmids were extracted from the transformed strain and those plasmids of which insertion of the serA fragment was confirmed by a PCR method were treated with restriction enzyme EcoRI and ligated to the shuttle vector pVK. Determination of the base sequence of the product suggested that no full-length sequence be contained on the C-terminal side. The sequence thus obtained corresponds to the region from 277 bases upstream of SEQ ID NO: 13 on the 5' side to the 1134th base of SEQ ID NO: 13 in the Sequence Listing on the 3' side.

To obtain a fragment containing the full length serA gene, cloning of a deleted part from the chromosomal DNA of *Brevibacterium flavum* AJ13327 strain was performed according to the annexed protocol using TaKaRa LA PCR in vitro Cloning Kit (manufactured by Takara Shuzo Co., Ltd.)

First, the chromosomal DNA thus prepared was completely digested with various restriction enzymes and ligated with cassettes having respective restriction enzyme sites corresponding thereto. Cassette primer (C1) (SEQ ID NO: 5 in the Sequence Listing) and a primer complementary to a known region of DNA (S1) (SEQ ID NO: 6 in the Sequence Listing) were used for carrying out first PCR. Using a portion of the reaction mixture, second PCR was carried out with inner primer C2 (SEQ ID NO: 7 in the Sequence Listing) and S2 (SEQ ID NO: 8 in the Sequence Listing) to amplify only the targeted DNA.

When EcoRI (manufactured by Takara Shuzo Co., Ltd.) was used as the restriction enzyme, the amplification of the targeted DNA was confirmed and the base sequence of the PCR product was determined directly. Based on the base sequence thus obtained, a primer coding for the C-terminal side was made and the fragments containing full length serA were collected from *Brevibacterium flavum* ATCC 14067 as a wild type strain and *Brevibacterium flavum* AJ13327 as a mutant strain. SEQ ID NOS: 9 and 10 in the Sequence Listing show the sequences of N-terminal and C-terminal side DNA primers, respectively.

The gene fragments containing wild type serA and mutant serA, respectively, in their full length were ligated to EcoRI-cleaved shuttle vector pVK7 using Original TA cloning Kit (manufactured by Invitrogen). Plasmids harboring respective gene fragments were made separately and their base sequence was determined. SEQ ID NOS: 11 and 13 indicate the sequences of the wild type and of mutant, respectively. SEQ ID NOS: 12 and 14 indicate amino acid sequences that these sequences can code for. Comparing the base sequences thus determined, it was confirmed that in the mutant serA, the 1087th base, G, was mutated into A and as a result, the 325th amino acid, glutamic acid, was changed to lysine.

Example 6
Introduction of Plasmid Containing 3-PGDH Gene into *Brevibacterium flavum*

Plasmids harboring wild type serA or mutant serA were each introduced into *Brevibacterium flavum* AJ13377. The plasmids were introduced by the electric pulse method (Sugimoto et al., Japanese Patent Application Laid-open No. 2-207791). Transformed cells were selected in a complete medium containing 25 μg/ml of kanamycin.

Example 7
Production of L-serine by Transformed Cells

Transformed cells each having introduced therein plasmids harboring gene fragments containing wild serA or mutant serA in their full-length were incubated in a 500 ml shaking flask according to Example 3, and L-serine produced was determined. As a control, the AJ13377 strain as a host was incubated similarly.

In the transformed cell having introduced therein the wild type serA was observed no influence on its L-serine productivity whereas in the transformed cell having introduced therein the mutant serA was confirmed an increase in L-serine productivity (Table 3).

*Brevibacterium flavum* AJ13377 has been deposited since Oct. 15, 1997 in National Institute of Bioscience and Human Technology of Agency of Industrial Science and Technology of Ministry of International Trade and Industry (zip code: 305-8566, 1–3 Higashi 1-Chome, Tsukuba-shi, Ibaraki-ken, Japan), as accession number of FERM P-16471, and transferred from the original deposition to international deposition based on Budapest Treaty on Nov. 20, 1998, and has been deposited as accession number of FERM BP-6576.

Further, the plasmid containing the mutant serA was retained in *Brevibacterium flavum* ATCC 14067. The plasmid-retaining strain has been awarded *Brevibacterium flavum* AJ13378 and deposited since Oct. 15, 1997 in National Institute of Bioscience and Human Technology of Agency of Industrial Science and Technology of Ministry of International Trade and Industry (zip code: 305-8566, 1–3 Higashi 1-Chome, Tsukuba-shi, Ibaraki-ken, Japan), as accession number of FERM P-16472, and transferred from the original deposition to international deposition based on Budapest Treaty on Nov. 20, 1998, and has been deposited as accession number of FERM BP-6577.

Figure 3:
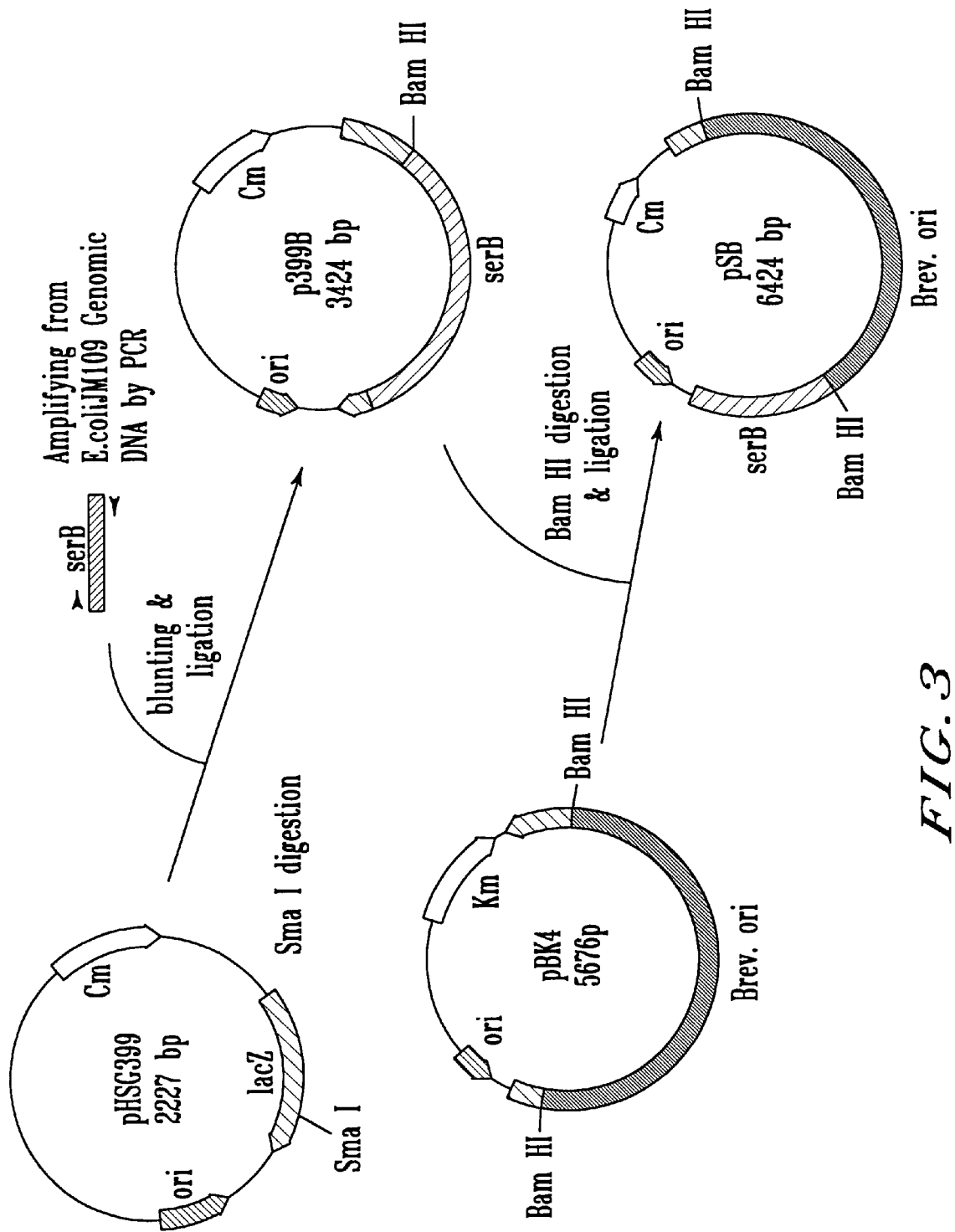
FIG. 3 illustrates the construction of plasmid pSB on which serB is carried.
Figure 4:
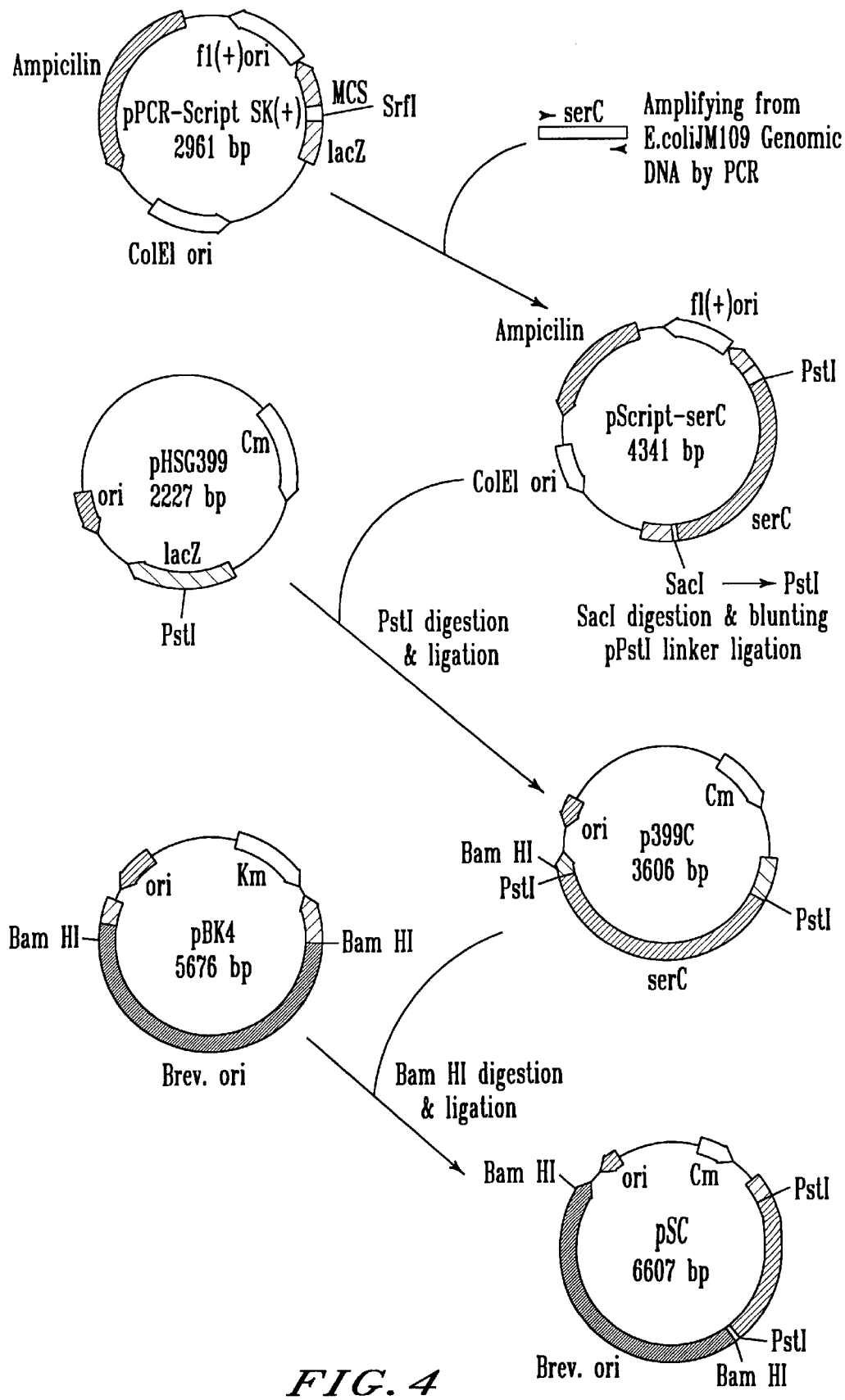
FIG. 4 illustrates the construction of plasmid pSC on which serC is carried.

Example 8
Amplification of serB and/or serC in *Brevibacterium flavum* L-serine Producing Strains
(1) Construction of Plasmid Expressing serB or serC Plasmids pSB that express serB and plasmids pSC that express serC were constructed as illustrated in FIGS. 3 and 4.

For the serB gene was made a primer (SEQ ID NOS: 15 and 16 in the Sequence Listing indicate N-terminal and C-terminal sides, respectively) based on the known base sequence (GenBank; X03046, M30784). On the other hand, for the serC gene, a primer (SEQ ID NOS: 17 and 18 in the Sequence Listing indicate N-terminal and C-terminal sides, respectively) was prepared based on the known base sequence (GenBank; D90728) and PCR was carried out using the chromosomal DNA of *Escherichia coli* JM109 as a template to obtain a gene fragment (1197 bp) containing ORF coding for serB and a gene fragment (1380 bp) containing ORF coding for serC.

The base sequences of SEQ ID NOS: 15 and 16 correspond to the regions of base Nos. 1197 to 1175 and of base Nos. 1 to 23 in the sequence GenBank; X03046, M30784 and the base sequences of SEQ ID NOS: 17 and 18 correspond to the regions of base Nos. 13205 to 13227 and of base Nos. 14584 to 14562 in the sequence GenBank; D90728.

The serB fragment, after blunt ended, was inserted into the SmaI site of pHSG399, a high copy type vector, to obtain p399B. To render this plasmid to be capable of autonomic replication in bacteria belonging to the genus Corynebacterium, a replicator (hereafter, referred to "Brev.-ori") was cleaved form pBK4 retaining the replicator derived from pHM1519 and inserted to p399B to obtain pSB (FIG. 3). pBK4 was made as follows. That is, a plasmid pHC4 containing Brev.-ori was prepared from *Escherichia coli* AJ12617 strain containing this plasmid (FERM BP-3532) and cleaved with KpnI (manufactured by Takara Shuzo Co., Ltd.) and BamHI (manufactured by Takara Shuzo Co., Ltd.) to extract Brev.-ori fragment, which was then blunt ended. Blunting of the ends was carried out using DNA Blunting Kit (manufactured by Takara Shuzo Co., Ltd.) according to the prescribed method. Thereafter, the product was ligated to an already phosphorylated BamHI linker and cleaved again with BamHI. This was ligated to pHSG298 that was also cleaved with BamHI to obtain pBK4. pBK4 may be used for cleaving Brev.-ori fragment with BamHI.

Further, a serC fragment was inserted to the SrfI site of pPCR-Script SK(+) to obtain pScript-serC. To the SacI site of the resulting plasmid was inserted a PstI linker. Then, the serC fragment was cleaved with PstI and inserted to the PstI site of pHSG399 to obtain p399C. A replicator was cleaved from pBK4 retaining the replicator derived from pHM1519 and inserted into p399C to obtain pSC (FIG. 4).

(2) Construction of Plasmid that Expresses serB and serC

Figure 5:
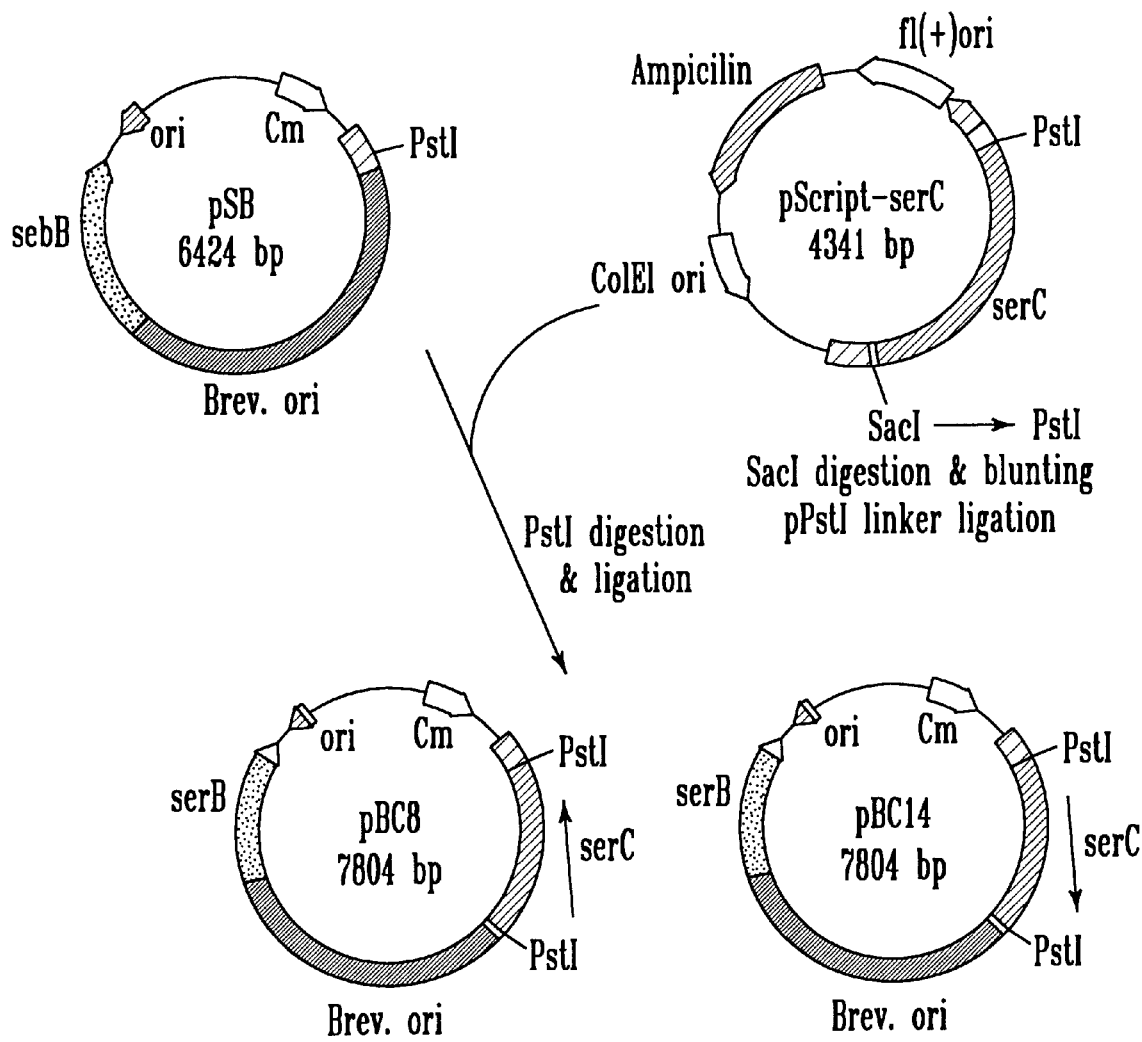
FIG. 5 illustrates the construction of plasmid pBC8 and pBC14 on which serB and serC are carried.

Next, plasmids pBC8 and pBC14 that express serB and serC, respectively, were made (FIG. 5). To the SacI site existing outside the serC fragment of the above-described pScript-serC was inserted a PstI linker to introduce a PstI site. This plasmid was treated with PstI to cleave a serC fragment, which was then inserted to the PstI site of the serB-containing plasmid pSB. The base sequence was confirmed and the plasmid in which the serC fragment was inserted in the reverse direction to lacZ was named pBC8, and the plasmid in which it was inserted in the forward direction to lacZ was named pBC14.

(3) L-Serine Production by serB and serC Amplified Strains

Using the plasmids pSB, pSC and pBC8 made as described above, the wild type strain of *Brevibacterium flavum* ATCC 14067 was transformed and plasmids were extracted from the transformed cells. The plasmids were used for transforming *Brevibacterium flavum* AJ13377 and AJ13327 having L-serine productivity. Also, *Brevibacterium flavum* AJ13377 and AJ13327 strains retaining pBC8 were transformed with a plasmid containing the mutant serA that *Brevibacterium flavum* AJ13378 (FERM P-16472) retained.

Each of the transformed strains was incubated on an agar medium containing 10 mg/L of chloramphenicol and the colonies formed were each incubated in the same manner as in Example 3, followed by measurement of L-serine that accumulated in the medium. The transformed strains that contained mutant serA were incubated by adding 25 mg/L of kanamycin to the medium. Table 3 shows the results obtained.

TABLE 3

| Strain | Amplified Gene | Amount of L-serine that accumulated (g/L) |
|---|---|---|
| AJ13377 | — | 5.0 |
| | serA | 5.0 |
| | serA* | 12.0 |
| | serB | 19.3 |
| | serC | 8.3 |
| | serB,serC | 19.5 |
| | serA*,serB,serC | 24.8 |
| AJ13327 | — | 15.4 |
| | serB | 24.2 |
| | serC | 19.8 |
| | serB,serC | 26.4 |
| | serA*,serB,serC | 35.2 | serA*: Mutant serA gene

As described above, amplification of serB or serC increased the amount of L-serine that accumulated. Also, amplification of the both serB and serC genes further increased the amount of L-serine that accumulated. In addition, amplification of the genes together with mutant serA gene increased the amount of L-serine that accumulated more. Similar results were obtained by using pBC14 instead of pBC8.

In the present example, although L-serine decomposing activity deficient strain (AJ13377) or L-serine decomposing activity deficient, azaserine resistant strain (AJ13327) of *Brevibacterium flavum* was used as coryneform bacterium host having L-serine productivity for amplifying each gene, other azaserine resistant strain (AJ13324) or L-serine decomposing activity deficient, β-(2-thienyl)-DL-alanine resistant strain (AJ13325) may also be used.

What is claimed is:

1. A coryneform bacterium, wherein the bacterium produces L-serine and wherein the intracellular activity of at least one of phosphoserine phosphatase and the phosphoserine transaminase is enhanced.

2. The coryneform bacterium of claim 1, wherein the intracellular activity of both the phosphoserine phosphatase and the phosphoserine transaminase is enhanced.

3. The coryneform bacterium of claim 1, wherein the intracellular activity of the phosphoserine phosphatase is enhanced.

4. The coryneform bacterium of claim 1, wherein the intracellular activity of the phosphoserine transaminase is enhanced.

5. The coryneform bacterium of claim 1, wherein said bacterium produces L-serine due to a deficiency in L-serine decomposing activity.

6. The coryneform bacterium of claim 1, wherein said bacterium produces L-serine due to its resistance to L-serine analogue(s).

7. The coryneform bacterium of claim 1, wherein the intracellular activity of at least one of phosphoserine phosphatase and phosphoserine transaminase is enhanced by increasing the copy number of at least one of phosphoserine phosphatase and phosphoserine transaminase.

8. The coryneform bacterium of claim 1, wherein the copy number of both the phosphoserine phosphatase and phosphoserine transaminase is increased.

9. The coryneform bacterium of claim 1, wherein the copy number of the phosphoserine phosphatase is increased.

10. The coryneform bacterium of claim 1, wherein the copy number of the phosphoserine transaminase is increased.

11. The coryneform bacterium of claim 1, wherein a gene coding for D-3-phosphoglycerate dehydrogenase in which feedback inhibition by L-serine is desensitized had been introduced therein.

12. A method of producing L-serine, comprising:
cultivating the coryneform bacterium of claim 1 in a medium to accumulate L-serine in the medium, and
collecting the L-serine from the medium.

13. A method of producing L-serine, comprising:
cultivating the coryneform bacterium of claim 2 in a medium to accumulate L-serine in the medium, and
collecting the L-serine from the medium.

14. A method of producing L-serine, comprising:
cultivating the coryneform bacterium of claim 3 in a medium to accumulate L-serine in the medium, and
collecting the L-serine from the medium.

15. A method of producing L-serine, comprising:
cultivating the coryneform bacterium of claim 4 in a medium to accumulate L-serine in the medium, and
collecting the L-serine from the medium.

16. A method of producing L-serine, comprising:
cultivating the coryneform bacterium of claim 5 in a medium to accumulate L-serine in the medium, and
collecting the L-serine from the medium.

17. A method of producing L-serine, comprising:
cultivating the coryneform bacterium of claim 6 in a medium to accumulate L-serine in the medium, and
collecting the L-serine from the medium.
18. A method of producing L-serine, comprising:
cultivating the coryneform bacterium of claim 7 in a medium to accumulate L-serine in the medium, and
collecting the L-serine from the medium.
19. A method of producing L-serine, comprising:
cultivating the coryneform bacterium of claim 8 in a medium to accumulate L-serine in the medium, and
collecting the L-serine from the medium.
20. A method of producing L-serine, comprising:
cultivating the coryneform bacterium of claim 9 in a medium to accumulate L-serine in the medium, and
collecting the L-serine from the medium.
21. A method of producing L-serine, comprising:
cultivating the coryneform bacterium of claim 10 in a medium to accumulate L-serine in the medium, and
collecting the L-serine from the medium.
22. A method of producing L-serine, comprising:
cultivating the coryneform bacterium of claim 11 in a medium to accumulate L-serine in the medium, and
collecting the L-serine from the medium.

* * * * *

SEQUENCE LISTING

```
<160> NUMBER OF SEQ ID NOS: 18

<210> SEQ ID NO 1
<211> LENGTH: 1432
<212> TYPE: DNA
<213> ORGANISM: Corynebacterium glutamicum
<220> FEATURE:
<221> NAME/KEY: CDS
<222> LOCATION: (398)..(1432)

<400> SEQUENCE: 1
ggatccggac acacgtgaca aaattgtaga aaattggatg attttgtcac gcctgtctgg      60
tttagctctg gttcgggacg ggcgtggaat ggaggtagcg caccgagacc ttgacccgcg     120
gcccgacaag ccaaaagtcc ccaaaacaaa cccacctcgc cggagacgtg aataaaattc     180
gcagctcatt ccatcagcgt aaacgcagct ttttgcatgg tgagacacct ttgggggtaa     240
atctcacagc atgaatctct gggttagatg actttctggg tgggggaggg tttagaatgt     300
ttctagtcgc acgccaaaac ccggcgtgga cacgtctgca gccgacgcgg tcgtgcctgt     360
tgtaggcgga cattcctagt ttttccagga gtaactt gtg agc cag aat ggc cgt     415
                                          Val Ser Gln Asn Gly Arg
                                           1               5
```

```
ccg gta gtc ctc atc gcc gat aag ctt gcg cag tcc act gtt gac gcg      463
Pro Val Val Leu Ile Ala Asp Lys Leu Ala Gln Ser Thr Val Asp Ala
            10                  15                  20 ctt gga gat gca gta gaa gtc cgt tgg gtt gac gga cct aac cgc cca      511
Leu Gly Asp Ala Val Glu Val Arg Trp Val Asp Gly Pro Asn Arg Pro
        25                  30                  35 gaa ctg ctt gat gca gtt aag gaa gcg gac gca ctg ctc gtg cgt tct      559
Glu Leu Leu Asp Ala Val Lys Glu Ala Asp Ala Leu Leu Val Arg Ser
    40                  45                  50 gct acc act gtc gat gct gaa gtc atc gcc gct gcc cct aac ttg aag      607
Ala Thr Thr Val Asp Ala Glu Val Ile Ala Ala Ala Pro Asn Leu Lys
55                  60                  65                  70 atc gtc ggt cgt gcc ggc gtg ggc ttg gac aac gtt gac atc cct gct      655
Ile Val Gly Arg Ala Gly Val Gly Leu Asp Asn Val Asp Ile Pro Ala
                75                  80                  85 gcc act gaa gct ggc gtc atg gtt gct aac gca ccg acc tct aac att      703
Ala Thr Glu Ala Gly Val Met Val Ala Asn Ala Pro Thr Ser Asn Ile
            90                  95                 100 cac tct gct tgt gag cac gca att tct ttg ctg ctg tct act gct cgc      751
His Ser Ala Cys Glu His Ala Ile Ser Leu Leu Leu Ser Thr Ala Arg
       105                 110                 115 cag atc cct gct gct gat gcg acg ctg cgt gag ggc gag tgg aag cgg      799
Gln Ile Pro Ala Ala Asp Ala Thr Leu Arg Glu Gly Glu Trp Lys Arg
   120                 125                 130 tct tct ttc aac ggt gtg gaa att ttc gga aaa act gtc ggt atc gtc      847
Ser Ser Phe Asn Gly Val Glu Ile Phe Gly Lys Thr Val Gly Ile Val
135                 140                 145                 150 ggt ttt ggc cac att ggt cag ttg ttt gct cag cgt ctt gct gcg ttt      895
Gly Phe Gly His Ile Gly Gln Leu Phe Ala Gln Arg Leu Ala Ala Phe
                155                 160                 165 gag acc acc att gtt gct tac gat cct tac gcc aac cct gct cgt gca      943
Glu Thr Thr Ile Val Ala Tyr Asp Pro Tyr Ala Asn Pro Ala Arg Ala
            170                 175                 180 gct cag ctg aac gtt gag ttg gtt gag ttg gat gag ctg atg agc cgt      991
Ala Gln Leu Asn Val Glu Leu Val Glu Leu Asp Glu Leu Met Ser Arg
       185                 190                 195 tct gac ttt gtc acc att cac ctt cct aag acc aag gaa act gct ggc     1039
Ser Asp Phe Val Thr Ile His Leu Pro Lys Thr Lys Glu Thr Ala Gly
   200                 205                 210 atg ttt gat gcg cag ctc ctt gct aag tcc aag aag ggc cag atc atc     1087
Met Phe Asp Ala Gln Leu Leu Ala Lys Ser Lys Lys Gly Gln Ile Ile
215                 220                 225                 230 atc aac gct gct cgt ggt ggc ctt gtt gat gag cag gct ttg gct gat     1135
Ile Asn Ala Ala Arg Gly Gly Leu Val Asp Glu Gln Ala Leu Ala Asp
                235                 240                 245 gcg att gag tcc ggt cac att cgt ggc gct ggt ttc gat gtg tac tcc     1183
Ala Ile Glu Ser Gly His Ile Arg Gly Ala Gly Phe Asp Val Tyr Ser
            250                 255                 260 acc gag cct tgc act gat tct cct ttg ttc aag ttg cct cag gtt gtt     1231
Thr Glu Pro Cys Thr Asp Ser Pro Leu Phe Lys Leu Pro Gln Val Val
       265                 270                 275 gtg act cct cac ttg ggt gct tct act gaa gag gct cag gat cgt gcg     1279
Val Thr Pro His Leu Gly Ala Ser Thr Glu Glu Ala Gln Asp Arg Ala
   280                 285                 290 ggt act gac gtt gct gat tct gtg ctc aag gcg ctg gct ggc gag ttc     1327
Gly Thr Asp Val Ala Asp Ser Val Leu Lys Ala Leu Ala Gly Glu Phe
295                 300                 305                 310 gtg gcg gat gct gtg aac gtt tcc ggt ggt cgc gtg ggc gaa gag gtt     1375
Val Ala Asp Ala Val Asn Val Ser Gly Gly Arg Val Gly Glu Glu Val
```

```
                       315                 320                 325
gct gtg tgg atg gat ctg gct cgc aag ctt ggt ctt ctt gct ggc aag            1423
Ala Val Trp Met Asp Leu Ala Arg Lys Leu Gly Leu Leu Ala Gly Lys
            330                 335                 340 ctt gtc gac                                                                1432
Leu Val Asp
        345

<210> SEQ ID NO 2
<211> LENGTH: 345
<212> TYPE: PRT
<213> ORGANISM: Corynebacterium glutamicum

<400> SEQUENCE: 2

Val Ser Gln Asn Gly Arg Pro Val Val Leu Ile Ala Asp Lys Leu Ala
 1               5                  10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Ala Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270

Lys Leu Pro Gln Val Val Thr Pro His Leu Gly Ala Ser Thr Glu
        275                 280                 285

Glu Ala Gln Asp Arg Ala Gly Thr Asp Val Ala Asp Ser Val Leu Lys
    290                 295                 300

Ala Leu Ala Gly Glu Phe Val Asp Ala Val Asn Val Ser Gly Gly
305                 310                 315                 320

Arg Val Gly Glu Glu Val Ala Val Trp Met Asp Leu Ala Arg Lys Leu
```

```
                          325                 330                 335
Gly Leu Leu Ala Gly Lys Leu Val Asp
                340                 345

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 3
ggacacacgt gacaaaattg tag                                          23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 4
gccagcaaga agaccaagct tgc                                          23

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 5
gtacatattg tcgttagaac gcgtaatacg actca                             35

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 6
tcatcaacgc tgctcgtggt ggc                                          23

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:Primer

<400> SEQUENCE: 7
cgttagaacg cgtaatacga ctcactatag ggaga                             35

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 8
gacgttgctg attctgtgct caa                                          23

<210> SEQ ID NO 9
```

-continued

```
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 9
gggagggttt agaatgtttc tag                                            23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 10
ggttcaagca aatggatctc taa                                            23

<210> SEQ ID NO 11
<211> LENGTH: 1730
<212> TYPE: DNA
<213> ORGANISM: Brevibacterium flavum
<220> FEATURE:
<221> NAME/KEY: CDS
<222> LOCATION: (115)..(1704)

<400> SEQUENCE: 11
gggagggttt agaatgtttc tagtcgcacg ccaaaacccg gcgtggacac gtctgcagcc    60
gacgcggtcg tgcctgttgt aggcggacat tcctagtttt tccaggagta actt gtg    117
                                                             Val
                                                              1 agc cag aat ggc cgt ccg gta gtc ctc atc gcc gat aag ctt gcg cag    165
Ser Gln Asn Gly Arg Pro Val Val Leu Ile Ala Asp Lys Leu Ala Gln
        5                   10                  15 tcc act gtt gac gcg ctt gga gat gca gta gaa gtc cgt tgg gtt gac    213
Ser Thr Val Asp Ala Leu Gly Asp Ala Val Glu Val Arg Trp Val Asp
    20                  25                  30 gga cct aac cgc cca gaa ctg ctt gat aca gtt aag gaa gcg gac gca    261
Gly Pro Asn Arg Pro Glu Leu Leu Asp Thr Val Lys Glu Ala Asp Ala
 35                  40                  45 ctg ctc gtg cgt tct gct acc act gtc gat gct gaa gtc atc gcc gct    309
Leu Leu Val Arg Ser Ala Thr Thr Val Asp Ala Glu Val Ile Ala Ala
 50                  55                  60                  65 gcc cct aac ttg aag atc gtc ggt cgt gcc ggc gtg ggc ttg gac aac    357
Ala Pro Asn Leu Lys Ile Val Gly Arg Ala Gly Val Gly Leu Asp Asn
                 70                  75                  80 gtt gac atc cct gct gcc act gaa gct ggc gtc atg gtt gct aac gca    405
Val Asp Ile Pro Ala Ala Thr Glu Ala Gly Val Met Val Ala Asn Ala
             85                  90                  95 ccg acc tct aac att cac tct gct tgt gag cac gca att tct ttg ctg    453
Pro Thr Ser Asn Ile His Ser Ala Cys Glu His Ala Ile Ser Leu Leu
        100                 105                 110 ctg tct act gct cgc cag atc cct gct gct gat gcg acg ctg cgt gag    501
Leu Ser Thr Ala Arg Gln Ile Pro Ala Ala Asp Ala Thr Leu Arg Glu
    115                 120                 125 ggc gag tgg aag cgg tct tct ttc aac ggt gtg gaa att ttc gga aaa    549
Gly Glu Trp Lys Arg Ser Ser Phe Asn Gly Val Glu Ile Phe Gly Lys
130                 135                 140                 145 act gtc ggt atc gtc ggt ttt ggc cac att ggt cag ttg ttt gct cag    597
Thr Val Gly Ile Val Gly Phe Gly His Ile Gly Gln Leu Phe Ala Gln
                150                 155                 160
```

-continued

| | | |
|---|---|---|
| cgt ctt gct gcg ttt gag acc acc att gtt gct tac gat cct tac gct<br>Arg Leu Ala Ala Phe Glu Thr Thr Ile Val Ala Tyr Asp Pro Tyr Ala<br>              165                    170                  175 | 645 |
| aac cct gct cgt gcg gct cag ctg aac gtt gag ttg gtt gag ttg gat<br>Asn Pro Ala Arg Ala Ala Gln Leu Asn Val Glu Leu Val Glu Leu Asp<br>180                    185                    190 | 693 |
| gag ctg atg agc cgt tct gac ttt gtc acc att cac ctt cct aag acc<br>Glu Leu Met Ser Arg Ser Asp Phe Val Thr Ile His Leu Pro Lys Thr<br>     195                    200                    205 | 741 |
| aag gaa act gct ggc atg ttt gat gcg cag ctc ctt gct aag tcc aag<br>Lys Glu Thr Ala Gly Met Phe Asp Ala Gln Leu Leu Ala Lys Ser Lys<br>210                    215                    220                    225 | 789 |
| aag ggc cag atc atc atc aac gct gct cgt ggt ggc ctt gtt gat gaa<br>Lys Gly Gln Ile Ile Ile Asn Ala Ala Arg Gly Gly Leu Val Asp Glu<br>                    230                    235                    240 | 837 |
| cag gct ttg gct gat gcg att gag tcc ggt cac att cgt ggc gct ggt<br>Gln Ala Leu Ala Asp Ala Ile Glu Ser Gly His Ile Arg Gly Ala Gly<br>              245                    250                    255 | 885 |
| ttc gat gtg tac tcc acc gag cct tgc act gat tct cct ttg ttc aag<br>Phe Asp Val Tyr Ser Thr Glu Pro Cys Thr Asp Ser Pro Leu Phe Lys<br>                    260                    265                    270 | 933 |
| ttg cct cag gtt gtt gtg act cct cac ttg ggt gct tct act gaa gag<br>Leu Pro Gln Val Val Val Thr Pro His Leu Gly Ala Ser Thr Glu Glu<br>275                    280                    285 | 981 |
| gct cag gat cgt gcg ggt act gac gtt gct gat tct gtg ctc aag gcg<br>Ala Gln Asp Arg Ala Gly Thr Asp Val Ala Asp Ser Val Leu Lys Ala<br>290                    295                    300                    305 | 1029 |
| ctg gct ggc gag ttc gtg gcg gat gct gtg aac gtt tcc ggt ggt cgc<br>Leu Ala Gly Glu Phe Val Ala Asp Ala Val Asn Val Ser Gly Gly Arg<br>                    310                    315                    320 | 1077 |
| gtg ggc gaa gag gtt gct gtg tgg atg gat ctg gct cgc aag ctt ggt<br>Val Gly Glu Glu Val Ala Val Trp Met Asp Leu Ala Arg Lys Leu Gly<br>              325                    330                    335 | 1125 |
| ctt ctt gct ggc aag ctt gtc gac gcc gcc cca gtc tcc att gag gtt<br>Leu Leu Ala Gly Lys Leu Val Asp Ala Ala Pro Val Ser Ile Glu Val<br>            340                    345                    350 | 1173 |
| gag gct cga ggc gag ctt tct tcc gag cag gtc gat gca ctt ggt ttg<br>Glu Ala Arg Gly Glu Leu Ser Ser Glu Gln Val Asp Ala Leu Gly Leu<br>355                    360                    365 | 1221 |
| tcc gct gtt cgt ggt ttg ttc tcc gga att atc gaa gag tcc gtt act<br>Ser Ala Val Arg Gly Leu Phe Ser Gly Ile Ile Glu Glu Ser Val Thr<br>370                    375                    380                    385 | 1269 |
| ttc gtc aac gct cct cgc att gct gaa gag cgt ggc ctg gac atc tcc<br>Phe Val Asn Ala Pro Arg Ile Ala Glu Glu Arg Gly Leu Asp Ile Ser<br>                    390                    395                    400 | 1317 |
| gtg aag acc aac tct gag tct gtt act cac cgt tcc gtc ctg cag gtc<br>Val Lys Thr Asn Ser Glu Ser Val Thr His Arg Ser Val Leu Gln Val<br>              405                    410                    415 | 1365 |
| aag gtc att act ggc agc ggc gcg agc gca act gtt gtt ggt gcc ctg<br>Lys Val Ile Thr Gly Ser Gly Ala Ser Ala Thr Val Val Gly Ala Leu<br>            420                    425                    430 | 1413 |
| act ggt ctt gag cgc gtt gag aag atc acc cgc atc aat ggc cgt ggc<br>Thr Gly Leu Glu Arg Val Glu Lys Ile Thr Arg Ile Asn Gly Arg Gly<br>435                    440                    445 | 1461 |
| ctg gat ctg cgc gca gag ggt ctg aac ctc ttc ctg cag tac act gac<br>Leu Asp Leu Arg Ala Glu Gly Leu Asn Leu Phe Leu Gln Tyr Thr Asp<br>450                    455                    460                    465 | 1509 |
| gct cct ggt gca ctg ggt acc gtt ggt acc aag ctg ggt gct gct ggc<br>Ala Pro Gly Ala Leu Gly Thr Val Gly Thr Lys Leu Gly Ala Ala Gly<br>                    470                    475                    480 | 1557 |

```
atc aac atc gag gct gct gcg ttg act cag gct gag aag ggt gac ggc    1605
Ile Asn Ile Glu Ala Ala Ala Leu Thr Gln Ala Glu Lys Gly Asp Gly
            485                 490                 495 gct gtc ctg atc ctg cgt gtt gag tcc gct gtc tcc gaa gag ctg gaa    1653
Ala Val Leu Ile Leu Arg Val Glu Ser Ala Val Ser Glu Glu Leu Glu
        500                 505                 510 gct gaa atc aac gct gag ttg ggt gct act tcc ttc cag gtt gat ctt    1701
Ala Glu Ile Asn Ala Glu Leu Gly Ala Thr Ser Phe Gln Val Asp Leu
    515                 520                 525 gac taattagaga tccattttct agaacc                                   1730
Asp
530

<210> SEQ ID NO 12
<211> LENGTH: 530
<212> TYPE: PRT
<213> ORGANISM: Brevibacterium flavum

<400> SEQUENCE: 12

Val Ser Gln Asn Gly Arg Pro Val Val Leu Ile Ala Asp Lys Leu Ala
 1               5                  10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Thr Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
145                 150                 155                 160

Gln Arg Leu Ala Ala Phe Glu Thr Thr Ile Val Ala Tyr Asp Pro Tyr
                165                 170                 175

Ala Asn Pro Ala Arg Ala Ala Gln Leu Asn Val Glu Leu Val Glu Leu
            180                 185                 190

Asp Glu Leu Met Ser Arg Ser Asp Phe Val Thr Ile His Leu Pro Lys
        195                 200                 205

Thr Lys Glu Thr Ala Gly Met Phe Asp Ala Gln Leu Leu Ala Lys Ser
    210                 215                 220

Lys Lys Gly Gln Ile Ile Ile Asn Ala Ala Arg Gly Gly Leu Val Asp
225                 230                 235                 240

Glu Gln Ala Leu Ala Asp Ala Ile Glu Ser Gly His Ile Arg Gly Ala
                245                 250                 255

Gly Phe Asp Val Tyr Ser Thr Glu Pro Cys Thr Asp Ser Pro Leu Phe
            260                 265                 270

Lys Leu Pro Gln Val Val Val Thr Pro His Leu Gly Ala Ser Thr Glu
        275                 280                 285
```

-continued

```
Glu Ala Gln Asp Arg Ala Gly Thr Asp Val Ala Asp Ser Val Leu Lys
        290                 295                 300

Ala Leu Ala Gly Glu Phe Val Ala Asp Ala Val Asn Val Ser Gly Gly
305                 310                 315                 320

Arg Val Gly Glu Glu Val Ala Val Trp Met Asp Leu Ala Arg Lys Leu
                325                 330                 335

Gly Leu Leu Ala Gly Lys Leu Val Asp Ala Ala Pro Val Ser Ile Glu
            340                 345                 350

Val Glu Ala Arg Gly Glu Leu Ser Ser Glu Gln Val Asp Ala Leu Gly
        355                 360                 365

Leu Ser Ala Val Arg Gly Leu Phe Ser Gly Ile Ile Glu Glu Ser Val
    370                 375                 380

Thr Phe Val Asn Ala Pro Arg Ile Ala Glu Arg Gly Leu Asp Ile
385                 390                 395                 400

Ser Val Lys Thr Asn Ser Glu Ser Val Thr His Arg Ser Val Leu Gln
                405                 410                 415

Val Lys Val Ile Thr Gly Ser Gly Ala Ser Ala Thr Val Val Gly Ala
            420                 425                 430

Leu Thr Gly Leu Glu Arg Val Glu Lys Ile Thr Arg Ile Asn Gly Arg
        435                 440                 445

Gly Leu Asp Leu Arg Ala Glu Gly Leu Asn Leu Phe Leu Gln Tyr Thr
    450                 455                 460

Asp Ala Pro Gly Ala Leu Gly Thr Val Gly Thr Lys Leu Gly Ala Ala
465                 470                 475                 480

Gly Ile Asn Ile Glu Ala Ala Ala Leu Thr Gln Ala Glu Lys Gly Asp
                485                 490                 495

Gly Ala Val Leu Ile Leu Arg Val Glu Ser Ala Val Ser Glu Glu Leu
            500                 505                 510

Glu Ala Glu Ile Asn Ala Glu Leu Gly Ala Thr Ser Phe Gln Val Asp
        515                 520                 525

Leu Asp
    530
```

<210> SEQ ID NO 13
<211> LENGTH: 1730
<212> TYPE: DNA
<213> ORGANISM: Brevibacterium flavum
<220> FEATURE:
<221> NAME/KEY: CDS
<222> LOCATION: (115)..(1704)

<400> SEQUENCE: 13

```
gggagggttt agaatgtttc tagtcgcacg ccaaaacccg gcgtggacac gtctgcagcc        60
gacgcggtcg tgcctgttgt aggcggacat tcctagtttt tccaggagta actt gtg       117
                                                             Val
                                                              1 agc cag aat ggc cgt ccg gta gtc ctc atc gcc gat aag ctt gcg cag       165
Ser Gln Asn Gly Arg Pro Val Val Leu Ile Ala Asp Lys Leu Ala Gln
        5                   10                  15 tcc act gtt gac gcg ctt gga gat gca gta gaa gtc cgt tgg gtt gac       213
Ser Thr Val Asp Ala Leu Gly Asp Ala Val Glu Val Arg Trp Val Asp
    20                  25                  30 gga cct aac cgc cca gaa ctg ctt gat aca gtt aag gaa gcg gac gca       261
Gly Pro Asn Arg Pro Glu Leu Leu Asp Thr Val Lys Glu Ala Asp Ala
35                  40                  45 ctg ctc gtg cgt tct gct acc act gtc gat gct gaa gtc atc gcc gct       309
Leu Leu Val Arg Ser Ala Thr Thr Val Asp Ala Glu Val Ile Ala Ala
        50                  55                  60
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|  50 |     |     |     |     |  55 |     |     |     |     |  60 |     |     |     |     |  65 |      |
| gcc | cct | aac | ttg | aag | atc | gtc | ggt | cgt | gcc | ggc | gtg | ggc | ttg | gac | aac | 357  |
| Ala | Pro | Asn | Leu | Lys | Ile | Val | Gly | Arg | Ala | Gly | Val | Gly | Leu | Asp | Asn |      |
|     |     |     |  70 |     |     |     |     |  75 |     |     |     |     |  80 |     |     |      |
| gtt | gac | atc | cct | gct | gcc | act | gaa | gct | ggc | gtc | atg | gtt | gct | aac | gca | 405  |
| Val | Asp | Ile | Pro | Ala | Ala | Thr | Glu | Ala | Gly | Val | Met | Val | Ala | Asn | Ala |      |
|     |     |     |     |  85 |     |     |     |     |  90 |     |     |     |     |  95 |     |      |
| ccg | acc | tct | aac | att | cac | tct | gct | tgt | gag | cac | gca | att | tct | ttg | ctg | 453  |
| Pro | Thr | Ser | Asn | Ile | His | Ser | Ala | Cys | Glu | His | Ala | Ile | Ser | Leu | Leu |      |
|     |     |     | 100 |     |     |     |     | 105 |     |     |     |     | 110 |     |     |      |
| ctg | tct | act | gct | cgc | cag | atc | cct | gct | gct | gat | gcg | acg | ctg | cgt | gag | 501  |
| Leu | Ser | Thr | Ala | Arg | Gln | Ile | Pro | Ala | Ala | Asp | Ala | Thr | Leu | Arg | Glu |      |
|     |     | 115 |     |     |     |     | 120 |     |     |     |     | 125 |     |     |     |      |
| ggc | gag | tgg | aag | cgg | tct | tct | ttc | aac | ggt | gtg | gaa | att | ttc | gga | aaa | 549  |
| Gly | Glu | Trp | Lys | Arg | Ser | Ser | Phe | Asn | Gly | Val | Glu | Ile | Phe | Gly | Lys |      |
| 130 |     |     |     |     | 135 |     |     |     |     | 140 |     |     |     |     | 145 |      |
| act | gtc | ggt | atc | gtc | ggt | ttt | ggc | cac | att | ggt | cag | ttg | ttt | gct | cag | 597  |
| Thr | Val | Gly | Ile | Val | Gly | Phe | Gly | His | Ile | Gly | Gln | Leu | Phe | Ala | Gln |      |
|     |     |     |     | 150 |     |     |     |     | 155 |     |     |     |     | 160 |     |      |
| cgt | ctt | gct | gcg | ttt | gag | acc | acc | att | gtt | gct | tac | gat | cct | tac | gct | 645  |
| Arg | Leu | Ala | Ala | Phe | Glu | Thr | Thr | Ile | Val | Ala | Tyr | Asp | Pro | Tyr | Ala |      |
|     |     |     | 165 |     |     |     |     | 170 |     |     |     |     | 175 |     |     |      |
| aac | cct | gct | cgt | gcg | gct | cag | ctg | aac | gtt | gag | ttg | gtt | gag | ttg | gat | 693  |
| Asn | Pro | Ala | Arg | Ala | Ala | Gln | Leu | Asn | Val | Glu | Leu | Val | Glu | Leu | Asp |      |
|     |     | 180 |     |     |     |     | 185 |     |     |     |     | 190 |     |     |     |      |
| gag | ctg | atg | agc | cgt | tct | gac | ttt | gtc | acc | att | cac | ctt | cct | aag | acc | 741  |
| Glu | Leu | Met | Ser | Arg | Ser | Asp | Phe | Val | Thr | Ile | His | Leu | Pro | Lys | Thr |      |
|     | 195 |     |     |     |     | 200 |     |     |     |     | 205 |     |     |     |     |      |
| aag | gaa | act | gct | ggc | atg | ttt | gat | gcg | cag | ctc | ctt | gct | aag | tcc | aag | 789  |
| Lys | Glu | Thr | Ala | Gly | Met | Phe | Asp | Ala | Gln | Leu | Leu | Ala | Lys | Ser | Lys |      |
| 210 |     |     |     |     | 215 |     |     |     |     | 220 |     |     |     |     | 225 |      |
| aag | ggc | cag | atc | atc | atc | aac | gct | gct | cgt | ggt | ggc | ctt | gtt | gat | gaa | 837  |
| Lys | Gly | Gln | Ile | Ile | Ile | Asn | Ala | Ala | Arg | Gly | Gly | Leu | Val | Asp | Glu |      |
|     |     |     |     | 230 |     |     |     |     | 235 |     |     |     |     | 240 |     |      |
| cag | gct | ttg | gct | gat | gcg | att | gag | tcc | ggt | cac | att | cgt | ggc | gct | ggt | 885  |
| Gln | Ala | Leu | Ala | Asp | Ala | Ile | Glu | Ser | Gly | His | Ile | Arg | Gly | Ala | Gly |      |
|     |     |     | 245 |     |     |     |     | 250 |     |     |     |     | 255 |     |     |      |
| ttc | gat | gtg | tac | tcc | acc | gag | cct | tgc | act | gat | tct | cct | ttg | ttc | aag | 933  |
| Phe | Asp | Val | Tyr | Ser | Thr | Glu | Pro | Cys | Thr | Asp | Ser | Pro | Leu | Phe | Lys |      |
|     |     | 260 |     |     |     |     | 265 |     |     |     |     | 270 |     |     |     |      |
| ttg | cct | cag | gtt | gtt | gtg | act | cct | cac | ttg | ggt | gct | tct | act | gaa | gag | 981  |
| Leu | Pro | Gln | Val | Val | Val | Thr | Pro | His | Leu | Gly | Ala | Ser | Thr | Glu | Glu |      |
|     | 275 |     |     |     |     | 280 |     |     |     |     | 285 |     |     |     |     |      |
| gct | cag | gat | cgt | gcg | ggt | act | gac | gtt | gct | gat | tct | gtg | ctc | aag | gcg | 1029 |
| Ala | Gln | Asp | Arg | Ala | Gly | Thr | Asp | Val | Ala | Asp | Ser | Val | Leu | Lys | Ala |      |
| 290 |     |     |     |     | 295 |     |     |     |     | 300 |     |     |     |     | 305 |      |
| ctg | gct | ggc | gag | ttc | gtg | gcg | gat | gct | gtg | aac | gtt | tcc | ggt | ggt | cgc | 1077 |
| Leu | Ala | Gly | Glu | Phe | Val | Ala | Asp | Ala | Val | Asn | Val | Ser | Gly | Gly | Arg |      |
|     |     |     |     | 310 |     |     |     |     | 315 |     |     |     |     | 320 |     |      |
| gtg | ggc | gaa | aag | gtt | gct | gtg | tgg | atg | gat | ctg | gct | cgc | aag | ctt | ggt | 1125 |
| Val | Gly | Glu | Lys | Val | Ala | Val | Trp | Met | Asp | Leu | Ala | Arg | Lys | Leu | Gly |      |
|     |     |     | 325 |     |     |     |     | 330 |     |     |     |     | 335 |     |     |      |
| ctt | ctt | gct | ggc | aag | ctt | gtc | gac | gcc | gcc | cca | gtc | tcc | att | gag | gtt | 1173 |
| Leu | Leu | Ala | Gly | Lys | Leu | Val | Asp | Ala | Ala | Pro | Val | Ser | Ile | Glu | Val |      |
|     |     | 340 |     |     |     |     | 345 |     |     |     |     | 350 |     |     |     |      |
| gag | gct | cga | ggc | gag | ctt | tct | tcc | gag | cag | gtc | gat | gca | ctt | ggt | ttg | 1221 |
| Glu | Ala | Arg | Gly | Glu | Leu | Ser | Ser | Glu | Gln | Val | Asp | Ala | Leu | Gly | Leu |      |
|     | 355 |     |     |     |     | 360 |     |     |     |     | 365 |     |     |     |     |      |
| tcc | gct | gtt | cgt | ggt | ttg | ttc | tcc | gga | att | atc | gaa | gag | tcc | gtt | act | 1269 |

```
Ser Ala Val Arg Gly Leu Phe Ser Gly Ile Ile Glu Glu Ser Val Thr
370                 375                 380                 385 ttc gtc aac gct cct cgc att gct gaa gag cgt ggc ctg gac atc tcc        1317
Phe Val Asn Ala Pro Arg Ile Ala Glu Glu Arg Gly Leu Asp Ile Ser
                390                 395                 400 gtg aag acc aac tct gag tct gtt act cac cgt tcc gtc ctg cag gtc        1365
Val Lys Thr Asn Ser Glu Ser Val Thr His Arg Ser Val Leu Gln Val
        405                 410                 415 aag gtc att act ggc agc ggc gcg agc gca act gtt gtt ggt gcc ctg        1413
Lys Val Ile Thr Gly Ser Gly Ala Ser Ala Thr Val Val Gly Ala Leu
        420                 425                 430 act ggt ctt gag cgc gtt gag aag atc acc cgc atc aat ggc cgt ggc        1461
Thr Gly Leu Glu Arg Val Glu Lys Ile Thr Arg Ile Asn Gly Arg Gly
435                 440                 445 ctg gat ctg cgc gca gag ggt ctg aac ctc ttc ctg cag tac act gac        1509
Leu Asp Leu Arg Ala Glu Gly Leu Asn Leu Phe Leu Gln Tyr Thr Asp
450                 455                 460                 465 gct cct ggt gca ctg ggt acc gtt ggt acc aag ctg ggt gct gct ggc        1557
Ala Pro Gly Ala Leu Gly Thr Val Gly Thr Lys Leu Gly Ala Ala Gly
                470                 475                 480 atc aac atc gag gct gct gcg ttg act cag gct gag aag ggt gac ggc        1605
Ile Asn Ile Glu Ala Ala Ala Leu Thr Gln Ala Glu Lys Gly Asp Gly
                485                 490                 495 gct gtc ctg atc ctg cgt gtt gag tcc gct gtc tcc gaa gag ctg gaa        1653
Ala Val Leu Ile Leu Arg Val Glu Ser Ala Val Ser Glu Glu Leu Glu
        500                 505                 510 gct gaa atc aac gct gag ttg ggt gct act tcc ttc cag gtt gat ctt        1701
Ala Glu Ile Asn Ala Glu Leu Gly Ala Thr Ser Phe Gln Val Asp Leu
        515                 520                 525 gac taattagaga tccattttct agaacc                                       1730
Asp
530

<210> SEQ ID NO 14
<211> LENGTH: 530
<212> TYPE: PRT
<213> ORGANISM: Brevibacterium flavum

<400> SEQUENCE: 14

Val Ser Gln Asn Gly Arg Pro Val Val Leu Ile Ala Asp Lys Leu Ala
1               5                   10                  15

Gln Ser Thr Val Asp Ala Leu Gly Asp Ala Val Glu Val Arg Trp Val
            20                  25                  30

Asp Gly Pro Asn Arg Pro Glu Leu Leu Asp Thr Val Lys Glu Ala Asp
        35                  40                  45

Ala Leu Leu Val Arg Ser Ala Thr Thr Val Asp Ala Glu Val Ile Ala
    50                  55                  60

Ala Ala Pro Asn Leu Lys Ile Val Gly Arg Ala Gly Val Gly Leu Asp
65                  70                  75                  80

Asn Val Asp Ile Pro Ala Ala Thr Glu Ala Gly Val Met Val Ala Asn
                85                  90                  95

Ala Pro Thr Ser Asn Ile His Ser Ala Cys Glu His Ala Ile Ser Leu
            100                 105                 110

Leu Leu Ser Thr Ala Arg Gln Ile Pro Ala Ala Asp Ala Thr Leu Arg
        115                 120                 125

Glu Gly Glu Trp Lys Arg Ser Ser Phe Asn Gly Val Glu Ile Phe Gly
    130                 135                 140

Lys Thr Val Gly Ile Val Gly Phe Gly His Ile Gly Gln Leu Phe Ala
```

-continued

```
            145                 150                 155                 160
Gln Arg Leu Ala Ala Phe Glu Thr Thr Ile Val Ala Tyr Asp Pro Tyr
                    165                 170                 175
Ala Asn Pro Ala Arg Ala Ala Gln Leu Asn Val Glu Leu Val Glu Leu
            180                 185                 190
Asp Glu Leu Met Ser Arg Ser Asp Phe Val Thr Ile His Leu Pro Lys
        195                 200                 205
Thr Lys Glu Thr Ala Gly Met Phe Asp Ala Gln Leu Leu Ala Lys Ser
    210                 215                 220
Lys Lys Gly Gln Ile Ile Ile Asn Ala Ala Arg Gly Gly Leu Val Asp
225                 230                 235                 240
Glu Gln Ala Leu Ala Asp Ala Ile Glu Ser Gly His Ile Arg Gly Ala
                245                 250                 255
Gly Phe Asp Val Tyr Ser Thr Glu Pro Cys Thr Asp Ser Pro Leu Phe
            260                 265                 270
Lys Leu Pro Gln Val Val Thr Pro His Leu Gly Ala Ser Thr Glu
        275                 280                 285
Glu Ala Gln Asp Arg Ala Gly Thr Asp Val Ala Asp Ser Val Leu Lys
    290                 295                 300
Ala Leu Ala Gly Glu Phe Val Ala Asp Ala Val Asn Val Ser Gly Gly
305                 310                 315                 320
Arg Val Gly Glu Lys Val Ala Val Trp Met Asp Leu Ala Arg Lys Leu
                325                 330                 335
Gly Leu Leu Ala Gly Lys Leu Val Asp Ala Ala Pro Val Ser Ile Glu
            340                 345                 350
Val Glu Ala Arg Gly Glu Leu Ser Ser Glu Gln Val Asp Ala Leu Gly
        355                 360                 365
Leu Ser Ala Val Arg Gly Leu Phe Ser Gly Ile Ile Glu Glu Ser Val
    370                 375                 380
Thr Phe Val Asn Ala Pro Arg Ile Ala Glu Glu Arg Gly Leu Asp Ile
385                 390                 395                 400
Ser Val Lys Thr Asn Ser Glu Ser Val Thr His Arg Ser Val Leu Gln
                405                 410                 415
Val Lys Val Ile Thr Gly Ser Gly Ala Ser Ala Thr Val Gly Ala
            420                 425                 430
Leu Thr Gly Leu Glu Arg Val Glu Lys Ile Thr Arg Ile Asn Gly Arg
        435                 440                 445
Gly Leu Asp Leu Arg Ala Glu Gly Leu Asn Leu Phe Leu Gln Tyr Thr
    450                 455                 460
Asp Ala Pro Gly Ala Leu Gly Thr Val Gly Thr Lys Leu Gly Ala Ala
465                 470                 475                 480
Gly Ile Asn Ile Glu Ala Ala Leu Thr Gln Ala Glu Lys Gly Asp
                485                 490                 495
Gly Ala Val Leu Ile Leu Arg Val Glu Ser Ala Val Ser Glu Glu Leu
            500                 505                 510
Glu Ala Glu Ile Asn Ala Glu Leu Gly Ala Thr Ser Phe Gln Val Asp
        515                 520                 525
Leu Asp
    530

<210> SEQ ID NO 15
<211> LENGTH: 23
<212> TYPE: DNA
<213> ORGANISM: Artificial Sequence
```

-continued

```
<220> FEATURE:
<223> OTHER INFORMATION: Description of Artificial Sequence:Primer

<400> SEQUENCE: 15
ggcaagacag aacaggacaa tca                                            23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 16
agcttttgcc acggtgtacc tcg                                            23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 17
ccacattttt gccctcaacg gtt                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 18
cggttagaaa cgctcttgga acc                                            23
```